United States Patent [19]

Kise et al.

[11] Patent Number: 4,843,070
[45] Date of Patent: Jun. 27, 1989

[54] SUBSTITUTED THIAZETOQUINOLINE-3-CARBOXYLIC ACIDS AND PHARMACEUTICALLY ACCEPTABLE SALTS THEREOF

[75] Inventors: Masahiro Kise; Masahiko Kitano, both of Kyoto; Masakuni Ozaki, Joyo; Kenji Kazuno, Shige; Ichiro Shirahase, Kyoto; Yoshifumi Tomii, Katano; Jun Segawa, Kyoto, all of Japan

[73] Assignee: Nippon Shinyaku Co., Ltd., Japan

[21] Appl. No.: 49,814

[22] Filed: May 13, 1987

[30] Foreign Application Priority Data

May 14, 1986 [JP] Japan .................. 61-111620

[51] Int. Cl.$^4$ ................. C07D 513/04; A61K 31/495; A61K 31/425; A61K 31/55
[52] U.S. Cl. ..................... 514/210; 544/361; 544/60; 544/126; 544/392; 544/391; 544/395; 544/386; 544/374; 540/575; 540/599; 540/481; 546/80; 546/156; 558/17; 560/16
[58] Field of Search ................. 514/210, 254; 544/361, 544/365

[56] References Cited

U.S. PATENT DOCUMENTS 4,426,381 1/1984 Matsumura et al. ................. 514/254
4,620,007 10/1986 Grohe et al. ......................... 514/254
4,659,734 4/1987 Enomoto et al. ................... 514/255

FOREIGN PATENT DOCUMENTS 0058392 8/1982 European Pat. Off. ............ 544/361

59-210093 11/1984 Japan .
0227887 12/1984 Japan .................. 514/254

OTHER PUBLICATIONS

Derwent Abs. of J59210093.

Primary Examiner—Donald G. Daus
Assistant Examiner—E. Bernhardt
Attorney, Agent, or Firm—Jacobs & Jacobs

[57] ABSTRACT

Anti-bacterial and anti-fungal compounds of formula I and pharmaceutically acceptable salts thereof:

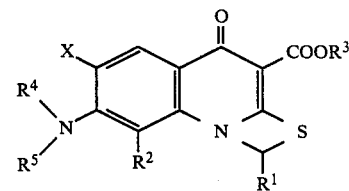

in which $R^1$ is hydrogen, alkyl or substituted or unsubstituted phenyl; $R^2$ is hydrogen, alkyl, alkoxy, hydroxy, halgen, nitro or substituted or unsubstituted amino; $R^3$ is hydrogen or substituted or unsubstituted alkyl; $R^4$ and $R^5$ are the same or different and are alkyl or hydroxyalkyl or $R^4$ and $R^5$ together with the nitrogen atom to which they are attached form an unsubstituted or substituted heterocyclic ring having the depicted nitrogen atom as the sole heteroatom or which may have nitrogen, oxygen or sulphur atoms as additional heteroatoms; and X is halogen.

75 Claims, No Drawings

SUBSTITUTED THIAZETOQUINOLINE-3-CARBOXYLIC ACIDS AND PHARMACEUTICALLY ACCEPTABLE SALTS THEREOF

The present invention relates to quinolinecarboxyic acid derivatives which are useful as therapuetic agents for various infectious diseases. More particularly, it relates to quinolinecarboxylic acid derivatives represented by formula (I) and pharmaceutically acceptable salts thereof:

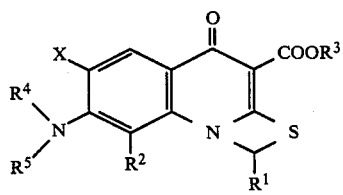

in which $R^1$ is hydrogen, alkyl or substituted or unsubstituted phenyl; $R^2$ is hydrogen, alkyl, alkoxy hydroxy, halogen, nitro or substituted or unsubstituted amino; $R^3$ is hydrogen or substituted or unsubstituted alkyl; $R^4$ and $R^5$ are the same or different and are alkyl or hydroxyalkyl or $R^4$ and $R^5$ together with the nitrogen atom to which they are attached form an unsubstituted or substituted heterocyclic ring having the depicted nitrogen atom as the sole heteroatom or which may have nitrogen, oxygen or sulphur atoms as additional heteroatoms; and X is halogen.

Synthetic antibacterial agents for use against Gram negative bacteria are of course known, and include nalidixic acid, piromidic acid, pipemidic acid, enoxacin (AT-2266), ofloxacin (DL-8280) and the like. However, such agents are not active against infections caused by Gram positive bacteria and Pseudomonas aeruginosa (chronic), which have been increasing recently and are hard to cure.

U.S. Pat. Nos. 4,426,381 and 4,659,734 disclose thiazoloquinolinecarboxylic acids as antibacterial agents and 7-chloro-6-fluoro-4-oxo-4H-(1,3)thiazeto(3,2-a)quinoline-3-carboxylic acid is disclosed as an intermediate. U.S. Pat. No. 4,550,104 also discloses thiazoloquinolinecarboxylic acid derivatives.

The present invention now provides new antibacterial agents of formula (I) which have the following characteristic features:

(1) There is a thiazetidine ring formed between the nitrogen and sulphur atom of the 2-mercaptoquinolone nucleus; and (2) The 6-position and 7-position of the compound of formula (I) are substituted with halogen and amine, respectively.

When $R^1$, $R^2$ and/or $R^3$ are alkyl, preferred examples are straight or branched chain alkyl having from about 1 to about 6 carbon atoms, such as methyl, ethyl, n-propyl, isopropyl, n-butyl, isobutyl, sec-butyl, tert-butyl, n-pentyl, isopentyl, n-hexyl, isohexyl, and the like.

When $R^1$ is substituted phenyl, it is preferred that $R^1$ is phenyl substituted by alkyl, alkoxy, hydroxy, halogen, trifluoromethyl, nitro, and the like. Preferably an alkyl substituent is straight or branched chain alkyl of from about 1 to about 6 carbon atoms and an alkoxy substituent is straight or branched alkoxy having from about 1 to about 4 carbon atoms, such as methoxy, ethoxy, n-propoxy, isopropoxy, n-butoxy, isobutoxy, sec-butoxy, tert-butoxy, and the like.

When $R^1$ is phenyl substituted by halogen or $R^2$ is halogen, it is preferred that halogen is chlorine, bromine, iodine, and fluorine, and most preferably fluorine.

When $R^2$ is alkoxy, it is preferred that $R^2$ is alkoxy having from about 1 to about 4 carbon atoms, examples of which are set forth above.

When $R^2$ is substituted amino, it is preferred that $R^2$ is acylamino in which the acyl moiety has from about 2 to about 6 carbon atoms, such as acetylamino, propionylamino, and the like.

When $R^3$ is substituted alkyl, it is preferred that $R^3$ is alkyl substituted by hydroxy, acyloxy of from about 2 to about 6 carbon atoms, acetyl, propionyl, n-butyryl, isobutyryl, valeryl, isovaleryl, pivaloyl, n-hexanoyl, etc., and alkoxy of from about 1 to about 4 carbon atoms, and the like, examples of which are provided above.

When X is halogen, X is preferably chlorine, bromine, iodine or fluorine, most preferably fluorine or chlorine.

When $R^4$ or $R^5$ is alkyl or hydroxyalkyl, it is preferred that the alkyl moiety is straight or branched alkyl having from about 1 to about 4 carbon atoms, such as methyl, ethyl, n-propyl, isopropyl, n-butyl, isobutyl, and the like. Preferred hydroxyalkyl includes 2-hydroxyethyl, 3-hydroxypropyl, 2-hydroxypropyl, and the like.

When $R^4$ and $R^5$ form a heterocyclic ring, it is preferred that the heterocyclic ring have from about 4 to about 8 ring members, which may further contain nitrogen, oxygen or sulphur atoms as additional heteroatoms therein. Examples of heterocyclic rings include azetidino, pyrrolidino, piperidino, azepino, azocino, piperazino, homopiperazino, pyrrolino, morpholino, thiomorpholino, imidazolino, imidazolidino, imidazolinino, pyrazolidino, pyrazolino, and the like.

If desired, the heterocyclic ring preferably has from one to three substituents, which may be the same or different. Examples of such substituents include alkyl, alkenyl, alkynyl, aryl, aralkyl, hydroxyalkyl, alkoxyalkyl, aminoalkyl, cyanoalkyl, carboalkoxyalkyl, acylalkyl, acyl, hydroxy, oxo, amino, alkylamino, dialkylamino, and the like. The alkyl substituent may include those exemplified for $R^1$ hereinabove. The alkenyl substituent may be straight or branched alkenyl having from about 2 to about 6 carbon atoms, such as vinyl, allyl, isopropenyl, 2-methallyl, 2-butenyl, 3-butenyl, and the like. Examples of alkynyl include straight or branched alkynyl having from about 2 to about 6 carbon atoms, such as ethynyl, 1-propynyl, and 2-propynyl. Examples of aryl include phenyl, alpha-naphthyl, beta-napthyl, biphenyl, and the like, most preferably phenyl. Examples of aralkyl include aralkyl having from about 7 to about 12 carbon atoms, such as benzyl, phenethyl, phenylpropyl, naphthylmethyl, and the like.

The hydroxyalkyl preferably has from about 1 to about 4 carbon atoms, such as hydroxymethyl, 2-hydroxyethyl, 3-hydroxypropyl, 2-hydroxypropyl, and the like, while alkoxyalkyl having from about 2 to about 6 carbon atoms is preferred, such as, for example, methoxyethyl, ethoxymethyl, and ethoxyethyl. The alkoxyalkyl may also be further substituted with hydroxyl. It is preferred that aminoalkyl has from about 1 to about 4 carbon atoms, such as aminomethyl, 2-aminoethyl, 3-aminopropyl, 4-aminobutyl, and the like. Cyanoalkyl having from about 2 to about 4 carbon atoms is preferred, such as cyanomethyl, 2-cyanoethyl, and 3-cyanopropyl. Carboalkoxyalkyl preferably has 1 to 4 carbon atoms in the alkoxy and alkyl moieties.

Acylalkyl having from about 3 to about 10 carbon atoms is preferred, such as acyl from about 2 to about 6 carbon atoms (as exemplified in the acyloxy for $R^2$) to which alkylene from about 1 to about 4 carbon atoms is combined. Such an acylalkyl may be further substituted with carboxy, carbomethoxy, carboethoxy, and the like. The acyl substituent preferably has from about 1 to about 6 carbon atoms, such as formyl as exemplified above.

The alkylamino substituent preferably has from about 1 to about 4 carbon atoms, such as methylamino, ethylamino, n-propylamino, isopropylamino, n-butylamino, and the like, and the dialkylamino preferably has from about 1 to about 4 carbon atoms in each alkyl moiety, such as dimethylamino, diethylamino, di-(n-propyl)amino and the like.

When any of the above substituents has a benzene ring, the benzene ring may be further substituted with alkoxy of from about 1 to about 4 carbon atoms or amino which is exemplified as hereinabove.

Examples of pharmaceutically acceptable salts of the compound (I) of the present invention are salts with mineral acids such as hydrochloric acid, sulfuric acid, nitric acid, phosphoric acid, hydrofluoric acid, hydrobromic acid, and the like, salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid, and the like, and salts with alkali metal or alkali earth metals such as sodium, potassium, calcium, and the like.

As to representative examples of the present invention, the following compounds, for example, may be listed in addition to the compounds given in the Examples.

Ethyl 6-fluoro-1-(4-fluorophenyl)-7-(4-methyl-1-piperazinyl)-4-oxo-4H-(1,3)thiazeto(3,2-a)quinoline-3-carboxylate; ethyl 6-fluoro-1-(4-fluorophenyl)-4-oxo-7-(1-piperazinyl)-4H-(1,3)thiazeto(3,2-a)quinoline-3-carboxylate; ethyl 6-fluoro-1-(4-fluorophenyl)-7-(3-methyl-1-piperazinyl)-4-oxo-4H-(1,3)thiazeto(3,2-a)quinoline-3-carboxylate; ethyl 6-fluoro-1-(4-fluorophenyl)-7-(3,4-dimethyl-1-piperazinyl)-4-oxo-4H-(1,3)thiazeto(3,2-a)quinoline-3-carboxylate; ethyl 1-(4-chlorophenyl)-6-fluoro-7-(4-methyl-1-piperazinyl)-4-oxo-4H-(1,3)thiazeto(3,2-a)quinoline-3-carboxylate; ethyl 1-(4-chlorophenyl)-6-fluoro-4-oxo-7-(1-piperazinyl)-4H-(1,3)thiazeto(3,2-a)quinoline-3-carboxylate; ethyl 1-(4-chlorophenyl)-6-fluoro-7-(3-methyl-1-piperazinyl)-4-oxo-4H-(1,3)thiazeto(3,2-a)quinoline-3-carboxylate; ethyl 1-(4-chlorophenyl)-6-fluoro-7-(3,4-dimethyl-1-piperazinyl)-4-oxo-4H-(1,3)thiazeto(3,2-a)quinoline-3-carboxylate; and 6-fluoro-8-methoxy-1-methyl-4-oxo-7(1piperazinyl)-4H-(1,3)thiazeto(3,2-a)quinoline-3-carboxylic acid (ethyl ester, m.p. 190° C. (decompn.)).

Presently preferred compounds include:
7-(4-acetonyl-1-piperazinyl)-6-fluoro-1-methyl-4-oxo-4H-(1,3)thiazeto(3,2-a)quinoline-3-carboxylic acid, and pharmaceutically acceptable salts thereof, including the methanesulfonate, hydrochloride and maleate thereof;

6-fluoro-1-methyl-4-oxo-7-(1-piperazinyl)-4H(1,3)thiazeto-(3,2-a)quinoline-3-carboxylic acid, and pharmaceutically acceptable salts thereof, including the methanesulfonate, hydrochloride and maleate thereof;

ethyl 6-fluoro-1-methyl-4-oxo-7-(1-piperazinyl)-4H-(1,3)-thiazeto(3,2-a)quinoline-3-carboxylate and pharmaceutically acceptable salts thereof, including the methanesulfonate, hydrochloride and maleate thereof;

ethyl 7-(4-acetonyl-1-piperazinyl)-6-fluoro-1-methyl-4-oxo-4H(1,3)thiazeto(3,2-a)quinoline-3-carboxylate, and pharmaceutically acceptable salts thereof, including the methanesulfonate, hydrochloride and maleate thereof;

6-fluoro-4-oxo-1-phenyl-7-(1-piperazinyl)-4H-(1,3)thiazeto(3,2-a)quinoline-3-carboxylic acid, and pharmaceutically acceptable salts thereof, including the methanesulfonate, hydrochloride and maleate thereof;

ethyl 6-fluoro-4-oxo-1-phenyl-7-(1-piperazinyl)-4H-(1,3)thiazeto(3,2-a)quinoline-3-carboxylate, and pharmaceutically acceptable salts thereof, including the methanesulfonate, hydrochloride and maleate thereof;

ethyl 6-fluoro-8-methoxy-1-methyl-7-(4-methyl-1-piperazinyl)4-oxo-4H-(1,3)thiazeto(3,2-a)quinoline-3-carboxylate and pharmaceutically acceptable salts thereof, including the methanesulfonate, hydrochloride and maleate thereof;

6-fluoro-8-methoxy-1-methyl-7-(4-methyl-1-piperazinyl)-4-oxo-4H-(1,3)thiazeto(3,2-a)quinoline-3-carboxylic acid and pharmaceutically acceptable salts thereof, including the methanesulfonate, hydrochloride and maleate thereof;

6-fluoro-7-(4-methyl-1-piperazinyl)-4-oxo-1-phenyl-4H-(1,3)thiazeto(3,2-a)quinoline-3-carboxlic acid, and pharmaceutically acceptable salts thereof, including the methanesulfonate, hydrochloride and maleate thereof;

ethyl 6-fluoro-7-(4-methyl-1-piperazinyl)-4-oxo-1-phenyl-4H-(1,3)thiazeto(3,2-a)quinoline-3-carboxylate and pharmaceutically acceptable salts thereof, including the methanesulfonate, hydrochloride and maleate thereof;

ethyl 6-fluoro-8-methoxy-1-methyl-4-oxo-7-(1-piperazinyl)-4H-(1,3)thiazeto(3,2-a)quinoline-3-carboxylate, and pharmaceutically acceptable salts thereof, including the methanesulfonate, hydrochloride and maleate thereof;

6-fluoro-8-methoxy-1-methyl-4-oxo-7-(1-piperazinyl)-4H-(1,3)thiazeto(3,2-a)quinoline-3-carboxylic acid or a pharmaceutically acceptable salt thereof.

The compounds of the present invention may, for example, be manufactured by the following methods:

Method A

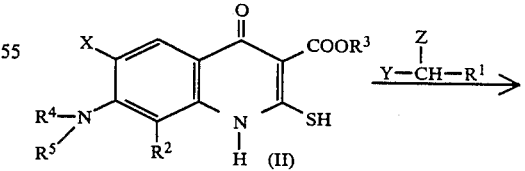

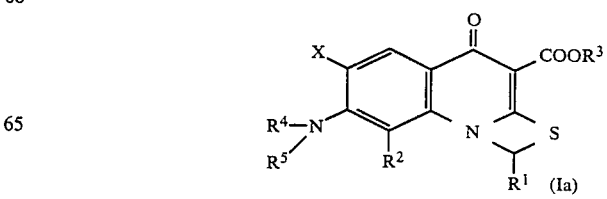

In the formulae, $R^1$, $R^2$, $R^4$, $R^5$ and X are the same as those already defined; Y and Z are same or different halogens; and $R^3$ is alkyl.

Method B

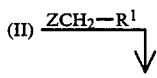

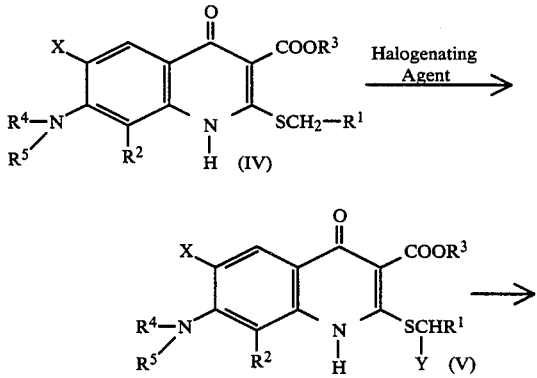

In the formulae, $R^1$, $R^2$, $R^3$, $R^4$, $R^5$, X, Y and Z are the same as those in the Method A.

Method C

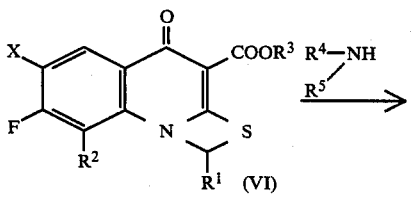

In the formulae, X, $R^1$, $R^2$, $R^3$, $R^4$, and $R^5$ are the same as those in the Method A.

Method D

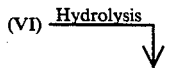

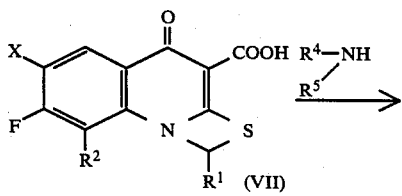

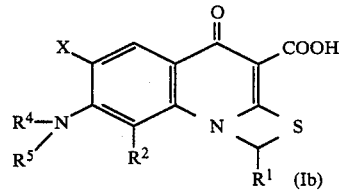

In the formulae X, $R^1$, $R^2$, $R^4$ and $R^5$ are the same as those hereinabove.

It will be apparent from the above description that the compounds of the present invention can be produced by two routes. One is to form a thiazetidine ring using quinolinecarboxylic acid substituted with an amino group at the 7-position of a starting material (Methods A and B) while the other is to form the thiazetidine ring followed by introducing an amino group in the 7-position (Methods C and D). These methods will be described in more detail below.

Method A: (II) and the dihalide, CHYZR¹, (e.g. methylene iodide, ethylidene bromide, benzylidene bromide, and the like) are reacted usually at 0° to 120° C., in the presence of an acid removing agent (e.g. sodium carbonate, potassium carbonate, triethylamine, etc.) in a solvent which is inert to the reaction whereupon cyclization results, giving (Ia). As to the solvent, nonprotonic solvent such as N,N-dimethylformamide, N,N-dimethylacetamide, dimethyl sulfoxide, sulfolane, and the like is preferred. The amounts of dihalide and acid removing agent are preferably not less than equimolar, and, more preferably 1.1 to 2.5 moles per mole of (II). In order to accelerate the reaction, the reaction may be conducted by addition of a catalytic amount (0.01 to 0.1 molar equivalent) of sodium iodide or potassium iodide.

Method B: (II) and the halide (ZCH₂R¹) are generally reacted at 0° to 80° C. using the same solvent and acid removing agent as in Method A to manufacture (IV). Then (IV) is halogenated with a halogenating agent (e.g. N-bromosuccinic imide, N-chlorosuccinic imide, and the like) in an inert solvent (e.g. chloroform, dichloromethane, carbon tetrachloride or other halogenated hydrocarbon type solvent) to give (V). Then (V) is cyclized generally at 0° to 80° C. by the use of the same solvent and acid removing agent as in Method A to afford (Ia).

Method C: (VI) is condensed with the amine (NHR⁴R⁵) to give (Ia). In this reaction, the amine is reacted in a solvent which is inert to the reaction (e.g. N,N-dimethylformamide, N,N-dimethylacetamide, dimethyl sulfoxide, sulfolane, acetonitrile, or other nonprotonic solvent) usually at 0° to 80° C. (e.g. 40° to 60° C.). The amount of the amine is 1.5 to 2.5 moles per mole of (VI).

Method D: (VI) is hydrolyzed using an acid (e.g. concentrated sulfuric acid, fuming sulfuric acid, polyphosphoric acid or a mixture thereof) to give (VII). This reaction is conducted using an excess (e.g. 1 to 30 times excess weight and, more preferably, 5 to 10 times excess by weight) of acid as a solvent usually at 0° to 60° C. This hydrolysis reaction may also be conducted in 20 to 30 times excess by weight (preferably 5 to 10 times excess by weight) of 1-5% potassium hydroxide or sodium hydroxide in aqueous alcohol (methanol, ethanol, propanol, butanol, and the like) generally at room temperature to 60° C. Then (VII) is reacted with the amine (NHR⁴R⁵) in the same solvent as used in Method C to give (Ib). The reaction is usually conducted at 0° to 60° C. and, more preferably, 0° C. to room temperature.

There are other methods, and one of them is to start from a compound of the general formula (VIII), whereby the product can be manufactured by the following route:

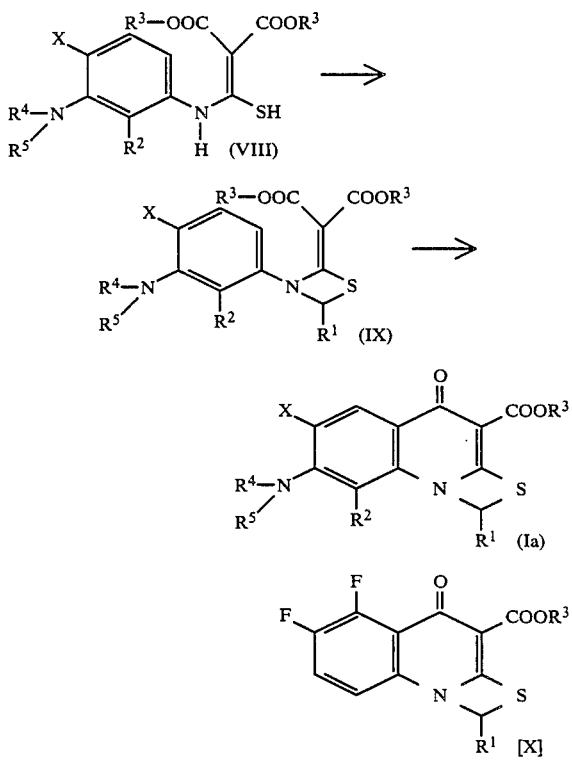

In the formulae, definitions for $R^1$, $R^2$, $R^3$, $R^4$, $R^5$ and X are the same as those in the Method A.

Thus, (VIII) and a dihalide are made to react in the presence of an acid removing agent (e.g. potassium carbonate) in an inert solvent (e.g. N,N-dimethylformamide). Then (IX) is subjected to a ring closure to manufacture (Ia). This ring closure reaction can be done by a known method known per se such as, for example, a method by heating and a method using acidic substance such as phosphorus oxychloride, phosphorus pentachloride, phosphorus trichloride, thionyl chloride, fuming sulfuric acid, concentrated sulfuric acid, polyphosphoric acid, polyphosphate, etc. When an acidic substance is applied, its amount is 1 mole to large excess (more preferably 20 to 30 moles) of acidic substance to 1 mole of (IX) and the reaction is usually conducted at 0° to 100° C. (more preferably at 0° to 60° C.). It is also possible that a thiazetidine ring is formed starting from 3,4-difluoro substance and then condensed with an amine by the same way as in the Method C to give (Ia). When $R^2$ is hydrogen, (X) is produced as a side product and, after removing it from the reaction mixture, the residue is made to react with an amine. Or the separation is carried out after the condensation with an amine.

When a diamine such as piperazine is used as a reactant in the above manufacturing methods, one of the amine groups is protected, if necessary, by a known method. The amine is made to react with (VI) and then the protective groups are detached to afford the desired compound (N-nonsubstituted compound). It is also possible that substituent(s) is(are) introduced to the nitrogen atom to the N-nonsubstituted compound by a known method per se to manufacture N-substituted diamino compound.

An 8-substituted derivative can also be manufactured by introduction of desired substituent(s) to the compound obtained hereinabove (where $R^2$ is hydrogen) by a method known per se.

When the compound manufactured by the above methods is an ester (i.e. $R^3$ is alkyl), it may be hydrolyzed, if desired, to give the corresponding carboxylic acid (i.e. $R^3$ is hydrogen). This hydrolysing reaction is conducted by the use of a large excess of acid (e.g. sulfuric acid, fumic sulfuric acid, hydrochloric acid, hydrobromic acid, hydrobromic acid/acetic acid, chlorosulfonic acid, polyphosphoric acid, and the like) and, more preferably 10 to 20 times excess of acid as a solvent, at room temperature to 110° C. Alternatively, the hydrolysis may also be conducted by stirring, at room temperature to 60° C., in a 1 to 5% aqueous alcohol (e.g., methanol, ethanol, propanol and butanol; among them, tert-butanol is preferred) of 20 to 30 times excess (preferably 5 to 10 times excess) of potassium hydroxide or sodium hydroxide.

Another method is to heat the ester with stirring at 60°-150° C., preferably at 100° to 110° C., in 10 to 100 times excess of alcohol corresponding to desired ester in the presence of a catalytic amount of concentrated sulfuric acid whereupon the desired ester can be afforded.

A carboxylic acid ($R^3$ is hydrogen), is, if desired, esterified to give an ester (e.g. $R^3$ is alkyl). In this esterification, an esterification method known per se may be used such as, for example, the use of thionyl chloride and alcohol; alcohol and condensing agent (e.g. dicyclocarbodiimide); or alkyl halide and alcoholate. In the case of the carboxylic acid, it may be used in a form pharmacologically-acceptable salt (e.g. sodium or potassium salts) by a known method per se.

Some of the starting compounds (II) and (VIII) are novel and such novel compounds may be manufactured by a known method (e.g. see U.S. Pat. No. 4,661,346) or by the same method as the Reference Examples given later.

Novel starting compounds (VI) are given later in Reference Examples and they are manufactured in the same or similar manner as the above Method A or Method B. The amine ($R^4R^5NH$) is a known substance or can be manufactured in a similar manner to known methods.

The desired compound (I) prepared as such can be separated and purified by various means known per se such as, for example, concentration, conversion of liquid properties, transfer to anothr solvent, extraction with a solvent, crystallization, recrystallization, fractional distillation, chromatography, and the like.

The compounds (I) of the invention are used to treat bacterial and fungal infections in animals, including humans, by administering to the sufferer an antibacterial or an anti-fungal effective amount of the compound (I) of the invention, preferably in the form of a pharmaceutical composition comprising an antibacterial or antifungal effective amount of the compound (I) in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses, or, alternatively, one half, third or foruth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the daily dosage for humans will be from about 50 to about 1000 mg., preferably from about 100 to about 300 mg. In some instances, a sufficient therapeutic effect can be obtained at a lower dose, while in others a large dose will be required.

While the routes of administration of the compound (I) of the invention include oral, parenteral (i.e., intramuscular, intraperitoneal and intravenous), topical and rectal, oral administration is particularly preferred.

The preferred pharmaceutical compositions are therefore those in a form suitable for oral administration, such as tablets and liquids.

The reference examples below illustrate compounds used in the manufacture of the compounds of the present invention.

REFERENCE EXAMPLE 1

Ethyl 6,7-difluoro-1-methyl-4-oxo-4H-(1,3)thiazeto(3,2-a)quinoline-3-carboxylate (1) 3,4-Difluoroaniline (600 g) and 1410 g of triethylamine were mixed and, with ice cooling and stirring, 389 g of carbon disulfide was dropped in during 2.5 hours. The mixture was stirred at the same temperature for 2 hours more whereupon crystals gradually appeared. The mixture was gradually warmed up to the room temperature, stirred for 2 hours, and kept in a refrigerator for two nights. Chloroform (2 liters) was added to the reaction mixture in which crystals were solidified, the mixture was stirred to make it suspended, and ethyl chloroformate was dropped in at 10° C. (inner temperature) during 2 hours. The mixture was stirred 3.5 hours more at room temperature. After the reaction, the reaction solution was poured over into ice water, the mixture was made weakly acidic with concentrated hydrochloric acid, and the chloroform layer was collected. This was washed with water, dried and concentrated and the residue was purified by a column chromatography (n-hexane/silica gel) to give 558.6 g of 3,4-difluorophenyl isothiocyanate in colorless oil.

(2) Ethyl malonate (200.3 g) was dropped into a stirring mixture of 2850 ml of dioxane and finely-powdered potassium hydroxide during 3 hours. After the dropping was completed, 186.2 g of oil obtained in (1) was dropped in at room temperature with stirring and then the mixture was stirred for 18 hours. Methoxymethyl chloride (100.2 g) was gradually dropped in with ice cooling and stirring, then stirred at room temperature for 3 hours, poured over into ice water, extracted with ethyl acetate, and the extract was washed with water and dried. The resulting residue was purified by a silica gel column chromatography (n-hexane/ethyl acetate (2:1) was used as an eluting solution) to give 383.8 g of oily diethyl 1-(3,4-difluorophenylamino)-1-(methoxymethylthio)-methylenemalonate.

(3) The oily substance (85.5 g) obtained in the above (2) was dissolved in 250 g of diphenyl ether and the solution was heated with stirring at 240° C. for 5 to 10 minutes. This was cooled to 80° C., poured over into 1 liter of n-hexane, and allowed to stand overnight in a cool place. Crystals separated out therefrom were collected by filtration and washed with n-hexane to give 195 g of ethyl 6,7-difluoro-4-hydroxy-2-methoxymethylthioquinoline-3-carboxylate, pale yellow crystals, m.p. 126°–129° C.

(4) Concentrated hydrochloric acid (600 ml) was dropped into a suspension of 195 g of the crystals obtained in (3) in 1 liter of ethanol at room temperature with stirring. After the dropping was completed, the mixture was stirred for 2 hours, ice water was added thereto, the crystals separated out therefrom were collected by filtration, washed with water and air-dried to give 166.6 g of ethyl 6,7-difluoro-4-hydroxy-2-mercaptoquinoline-3-carboxylate, yellow crystals, m.p. 201°–203° C. (decomposition).

(5) Ethylidene bromide (110.0 g), 77.4 g of potassium carbonate, 4.6 g of potassium iodide and 540 ml of N,N-dimethylformamide were placed in a flask and heated with stirring at 105°–110° C. A solution of 80 g of crystals obtained in (4) in 1400 ml of N,N-dimethylformamide was dropped into the above solution. After the dropping was completed, the mixture was stirred at the same temperature for 2.5 hours. After the reaction was completed, the mixture was concentrated in vacuo. The concentrated solution was poured over into ice water and crystals separated out were collected with filtration followed by washing with water and drying with air to give 61.4 g of ethyl 6,7-difluoro-1-methyl-4-oxo-4H-(1,3)thiazeto(3,2-a)quinoline-3-carboxylate as crude crystals. This was recrystallized from a 10:1 mixture of chloroform and methanol to give 41.2 g of colorless crystals. Melting point: 200°–202° C.

Elementary analysis calculated for $C_{14}H_{11}F_2NO_3S$.
Calcd (%): C 54.02, H 3.56, N 4.50.
Found (%): C 54.54, H 3.42, N 4.29.

REFERENCE EXAMPLE 2

(1) 2-Fluoro-6-methoxyaniline (7.80 g) and 17.23 g of di-(2-bromoethyl)amine hydrobromide were dissolved in 5 ml of water and, by heating at about 110° C. on a bath, 10 ml of 30% potassium hydroxide solution was added thereto (each about 3.5 ml once an hour). Heating was further continued (7 hours in total). After cooled, the reaction solution was made alkaline with aqueous solution of sodium hydroxide to salt out and extracted with chloroform twice. The extract was washed with saturated sodium chloride solution, dried over sodium sulfate, the solvent was evaporated therefrom, and the residue was purified by a column chromatography to give 8.95 g of oily 1-(2-fluoro-6-methoxyphenyl)piperazine in 34.94 g yield or 94%.

(2) The compound (34.89 g) obtained by the same manner as in the above (1) was dissolved in 50 g of formic acid and 135 g of 37% formaline and the solution was heated to reflux for 75 minutes at the bath temperature of 110° C. The reaction solution was concentrated in vacuo and dissolved in diluted hydrochloric acid.

Insoluble matters were removed, the residue was washed with ethyl acetate, made alkaline with aqueous solution of sodium hydroxide, salted out, and extracted with chloroform. The extract was dried over sodium sulfate and the solvent was evaporated therefrom. The residue was dissolved in ether, hydrochloric acid/ethanol was added thereto, and the hydrochloride was separated out therefrom. The crystals were washed with ether, dried, dissolved in water, sodium hydroxide solution was added, and extracted with ether. The extract was washed with saturated sodium chloride solution, dried over sodium sulfate, and the solvent was evaporated therefrom to give 26.18 g of oily 1-(2-fluoro-6-methoxyphenyl)-4-methylpiperazine, yield 70%.

(3) The compound (27.56 ) obtained by the same manner as in the above (2) and 42.14 g of silver sulfate were dissolved in 600 ml of concentrated sulfuric acid, a solution of 21.60 g of bromine in 1200 ml of concentrated sulfuric acid was dropped therein during about 30 minutes with ice-cooling, and the stirring was continued for another 90 minutes. The reaction solution was poured over into ice, the mixture was made alkaline with sodium hydroxide with ice cooling, and extracted with chloroform twice. The extract was washed with saturated sodium chloride solution and dried over sodium sulfate. The solvent was evaporated therefrom and purified by a column chromatography to give 14.12 g of 1-(3-bromo-2-fluoro-6-methoxyphenyl)-4-methylpiperazine. Yield 38%.

(4) The compound (13.42 g) obtained by the same manner as in the above (3) was dissolved in 500 ml of concentrated sulfuric acid and a solution of 4.70 g of potassium nitrate in 70 ml of concentrated sulfuric acid was dropped in during 20 minutes with ice-cooling (temperature being 4° to 6° C.). This was stirred for 30 minutes more, then poured over into ice water, the mixture was made weakly alkaline with sodium bicarbonate, and extracted with ethyl acetate. The extract was washed with saturated sodium chloride solution and dried over sodium sulfate. The solvent was evaported therefrom and purified with a column chromatography to give 3.29 g of 1-(3-bromo-2-fluoro-5-nitro-6-methoxyphenyl)-4-methylpiperazine. Yield 21%.

(5) The compound (2.778 g) obtained by the same manner as into the above (4) was dissolved in 60 ml of concentrated hydrochloric acid and a solution of 7.38 g of stannous chloride dihydrate in 80 ml of concentrated hydrochloric acid was dropped in with ice-cooling. After completion of the dropping, the mixture was stirred for 30 minutes more, poured over into ice, neutralized with diluted sodium hydroxide, and extracted with chloroform. The extract was washed with saturated sodium bicarbonate solution, dried over sodium sulfate, and the solvent was evaporated therefrom in vacuo. As a residue was obtained 2.432 g of 1-(5-amino-3-bromo-2-fluoro-6-methoxyphenyl)-4-methylpiperazine. Yield 96%.

(6) The compound (2.33 g) obtained by the same manner as in the above (5) was dissolved in 150 ml of ethanol, then 0.30 g of sodium hydroxide and 200 mg of 5% palladium-carbon were added, and the catalytic reduction was conducted at room temperature and ordinary pressure. The reaction solution was filtered and the filtrate was concentrated in vacuo. This was extracted with chloroform, the extract was washed with saturated sodium bicarbonate solution, dried over sodium sulfate and the sovlent was evaporated therefrom to give 1.68 g of 1-(5-amino-2-fluoro-6-methoxyphenyl)-4-methylpiperazine.

The following Examples also illustrate the present invention.

EXAMPLE 1

(1) 6-Fluoro-1-methyl-7-(4-methyl-1-piperazinyl)-4-oxo-4H-(1,3)thiazeto(3,2-a)quinoline-3-carboxylic acid.

To 50.0 g of cooling and stirring fuming sulfuric acid was little by little and gradually added 4.73 g of crystals of ethyl 6,7-difluoro-1-methyl-4-oxo-4H-(1,3)thiazeto(3,2-a)quinoline-3-carboxylate manufactured by the same manner as in (5) of the Reference Example 1 and dissolved in. The resulting solution was stirred at 60° C. for 30 minutes. The reaction solution was poured over into ice, the milky crystals separated out were centrifuged, washed with water, and air-dried to give 4.02 g of powdery crystals of 6,7-difluoro-1-methyl-4-oxo-4H-(1,3)thiazeto(3,2-a)quinoline-3-carboxylic acid. M.p. 269°–272° C. (decompn).

(2) A mixture of 14.1 g of crystals obtained in the above (1) and 300 ml of N,N-dimethylformamide was cooled in ice water and, with stirring, 10.6 g of N-methylpiperazine was gradually dropped in. After that, the mixture was stirred for 22 hours at room temperature. After the reaction, N,N-dimethylformamide was evaporated in vacuo. To the residue was added acetone and the crystals separated out were collected by filtration followed by washing with acetone, chloroform and ether to give 12.63 g of crystals of desired compound, m.p. 262° C. (decompn.).

Elementary analysis calculated for $C_{13}H_{18}FN_3O_3S$:
Calcd (%): C 56.18, H 4.99, N 11.56.
Found (%): C 56.17, H 5.18, N 11.48.

Hydrochloride melts at 288°–290° C. (decompn); sulfate melts at 252° C.; methanesulfonate melts at 251°–253° C. (decompn); toluenesulfonate melts at 265°–268° C. (decompn); 2-naphthalenesulfonate melts at 223°–225° C. (decompn); ethanesulfonate melts at 273°–275° C. (decompn); d-10-camphorsulfonate melts at 257°–259° C. (decompn); benzensulfonate melts at 246°–248° C. (decompn); maleate melts at 238°–240° C. (decompn,); and triphosphate melts at 201°–203° C. (decompn,).

Methanolic solution of sodium methylate was prepared from 0.126 g of sodium and 30 ml of anhydrous methanol and 2.0 g of the carboxylic acid as obtained above was added thereto followed by stirring for about 2 hours. The crystals separated out were collected by filtration after evaporation of methanol. The crystals were washed with methanol, acetone and ether and dried to give 2.1 g of sodium salt, m.p. 306°–309° C. (decompn.)

EXAMPLE 2

Ethyl 7-(4-acetyl-1-piperazinyl)-6-chloro-4-oxo-4H-(1,3)thiazeto(3,2-a)quinoline-3-carboxylate Into 50 ml of N,N-dimethylformamide were placed 2.35 g of methylene iodide and 2.5 g of potassium carbonate and a solution of 3.0 g of ethyl 7-(4-acetyl-1-piperazinyl)-6-chloro-4-hydroxy-2-mercaptoquinoline-3-carboxylate in 30 ml of N,N-dimethylformamide was gradually dropped in with stirring. After that, the mixture was stirred at room temperature for 1 hour, concentrated in vacuo, water was added to the residue, and insoluble crystals were collected by filtration. They were washed with water, dried, and recrystallized from a mixed solvent of ethanol and chloroform to give 2.49 g of colorless powdery crystals, m.p. 266°–268° C. (decompn).

Elementary analysis calculated for $C_{19}H_{20}ClN_3O_4S.\frac{1}{2}$ $H_2O$: Calcd (%): C 52.96, H 4.91, N 9.75. Found (%): C 53.16, H 4.69, N 9.69.

EXAMPLE 3

6-Chloro-1-methyl-7-(1-piperazinyl)-4-oxo-4H-(1,3)thiazeto(3,2-a)quinoline-3-carboxylic acid A mixture of 610 mg of ethyl 7-(4-acetyl-1-piperazinyl)-6-chloro-1-methyl-4-oxo-4H-(1,3)thiazeto(3,2-a)quinoline-3-carboxylate, 12 ml of 5% hydrochloric acid and 3 ml of ethanol was heated with stirring on an oil bath of 100°–110° C. for 2 hours. After cooling to about 50° C., this was neutralized with 5% ammonia water. Crystals separated out were collected by filtration, washed with water, dried and recrystallized from N,N-dimethylformamide to give pale yellow crystals, m.p. not lower than 300° C. (decompn).

Elementary analysis calculated for $C_{16}H_{16}ClN_3O_3S.1.5H_2O$: Calcd (%): C 48.92, H 4.87, N 10.70. Found (%): C 49.27, H 4.46, N 10.66.

NMR δ (DMSO-$d_6$): 2.10 (d, 3H), 2.90 (m, 4H), 3.10 (m, 4H), 6.40 (q, 1H), 7.01 (s, 1H), 8.10 (s, 1H), 8.00–9.00 (br, 1H).

EXAMPLE 4

Ethyl 6-fluoro-1-methyl-4-oxo-7-(1-piperazinyl)-4H-(1,3)thiazeto(3,2-a)quinoline-3-carboxylate Ethyl 6,7-difluoro-1-methyl-4-oxo-4H-(1,3)thiazeto(3,2-a)quinoline-3-carboxylate (5.0 g) was suspended in 150 ml of N,N-dimethylformamide and the suspension was stirred with 4.6 g of piperazine at room temperature for 48 hours. N,N-Dimethylformamide was evaporated in vacuo and to the residue was added ice water to collect the crystals by filtration. Purification by a column chromatography (silica gel/chloroform-methanol (1:1)) gave 3.0 g of desired compound, m.p. 224° C. (decompn.).

Elementary analysis calculated for $C_{18}H_{20}FN_3O_3S.\frac{3}{4}H_2O$. Calcd (%): C 55.30, H 5.54, N 10.74. Found (%): C 55.29, H 5.52, N 10.37.

EXAMPLE 5

Ethyl 7-(4-acetonyl-1-piperazinyl)-6-fluoro-1-methyl-4-oxo-4H-(1,3)thiazeto(3,2-a)quinoline-3-carboxylate Ethyl 6-fluoro-1-methyl-7-(1-piperazinyl)-4-oxo-4H-(1,3)thiazeto(3,2-a)quinoline-3-carboxylate (3.8 g) was suspended in 50 ml of N,N-dimethylformamide, 1.66 g of potassium carbonate was added thereto, 1.65 g of bromoacetone was dropped in with ice cooling and stirring, and the mixture was stirred at room temperature for 20 hours. The reaction solution was poured over into ice water and the crystals separated out were collected by filtration, washed with water, dried and recrystallized from ethanol to give 3.7 g of desired compound in colorless powdery crystals, m.p. 196°–200° C. (decompn.).

Elementary analysis calculated for $C_{21}H_{24}FN_3O_4S$: Calcd (%): C 58.18, H 5.58, N 9.69. Found (%): C 57.93, H 5.39, N 9.46.

EXAMPLE 6

7-(4-Acetyl-1-piperazinyl)-6-fluoro-4-oxo-4H-(1,3)thiazeto(3,2-a)quinoline-3-carboxylic acid (1) Sodium salt of ethyl 3-(4-acetyl-1-piperazinyl)-4-fluoro-phenylaminomercaptomethylenemalonate.

In 5 ml of dry tetrahydrofuran was suspended 0.173 g of sodium hydride, 0.57 g of diethyl malonate was dropped in with cooling and stirring, and the mixture was stirred for 30 minutes at room temperature. To this was added a solution of 1.0 g of 3-(4-acetyl-1-piperazinyl)-4-fluorophenyl isothiocyanate in 5.0 ml of dry tetrahydrofuran and the mixture was stirred at room temperature. After the reaction, the reaction solution was concentrated in vacuo and washed with ether to give 1.93 g of hygroscopic powder.

(2) Ethyl 3-(3-(4-acetyl-1-piperazinyl)-4-fluorophenyl)-(1,3)thiazetidin-2-ylidenemalonate.

The powder (1.66 g) obtained in (1) was dissolved in 10 ml of dry tetrahydrofuran. The solution was dropped into a solution of 1.16 g of methylene iodide and 0.60 g of potassium carbonate in 20 ml of N,N-dimethylformamide with stirring. The mixture was stirred at about 60° C. for 2 hours. The reaction solution was diluted with ice water and extracted with ethyl acetate. The extract was washed with water, dried and concentrated followed by crystallizing from ether to give 810 mg of colorless crystals, m.p. 136°–137° C.

(3) 7-(4-Acetyl-1-piperazinyl)-6-fluoro-4-oxo-4H-(1,3)thiazeto(3,2-a)quinoline-3-carboxylic acid and ethyl 7-(4-acetyl-1-pierazinyl)-6-fluoro-4-oxo-4H-(1,3)thiazeto(3,2-a)quinoline-3-carboxylate.

The crystals (800 mg) obtained in the above (2) were mixed with 30 g of polyphosphoric acid (PPA) and heated at 120° C. for 1 hour with stirring. The reaction solution was poured over into ice water and the crystals separated out were collected by filtration and washed with water and air-dried. Purification by a column chromatography (silica gel, chloroform-methanol (40:1→4:1)) gave 130 mg of the carboxylic acid (m.p. 247°–249° C., decompn.) and 180 mg of ethyl ester (m.p. 278°–280° C., decompn.).

(4) 7-(4-Acetyl-1-piperazinyl)-6-fluoro-4-oxo-4H-(1,3)thiazeto(3,2-a)quinoline-3-carboxylic acid.

Crystals (670 mg) obtained in the above (2) were dissolved in 10 g of fuming sulfuric acid with stirring and cooling and the solution was heated with stirring at 100° C. for 5 minutes. After cooling, the reaction product was poured over into ice, crystals separated out were collected by filtration, washed with water and dried to give 520 mg of colorless powdery crystals, m.p. 247°–249° C. (decompn.).

Elementary analysis calculated for $C_{17}H_{16}FN_3O_4S.\frac{1}{2}H_2O$: Calcd (%): C 52.84, H 4.43, N 10.87. Found (%): C 53.04, H 4.53, N 10.79.

EXAMPLE 7

6-Fluoro-7-(4-methyl-1-piperazinyl)-4-oxo-1-phenyl-4H-(1,3)thiazeto(3,2-a)quinoline-3-carboxylic acid Three grams of ethyl 6-fluoro-7-(4-methyl-1-piperazinyl)-4-oxo-1-phenyl-4H-(1,3)thiazeto(3,2-a)quinoline-3-carboxylate was suspended in 30 ml of mixed solution of 5% potassium hydroxide/tert-butanol-water (75:25) and the suspension was heated at 50° C. for 4 hours with stirring. To this was added 30 to 40 ml of water to prepare homogeneous solution. The solution was neutralized with acetic acid and extracted with chloroform to which small amount of methanol was added. The extract was dried, concentrated, and the resulting residue was recrystallized from ethanol to give desired product. Yield: 2.23 g. M.p. 216°–217° C. (decomp.).

The following compounds were prepared by similar manner as given in Examples 1 to 7.

6-Fluoro-7-(4-methyl-1-piperazinyl)-4-oxo-4H-(1,3)thiazeto(3,2-a)quinoline-3-carboxylic acid. M.p. not lower than 300° C. (decompn.).
IR$_{max}^{KBr}$ (cm$^{-1}$): 3400, 2800, 1700, 1625, 1600, 1485, 1375, 1300, 1250, 1230, 1110, 1010, 890, 805.

1-Ethyl-6-fluoro-7-(4-methyl-1-piperazinyl)-4-oxo-4H-(1,3)thiazeto(3,2-a)quinoline-3-carboxylic acid. M.p. 233°–234° C. (decompn.).

6-Fluoro-7-(1-piperazinyl)-4-oxo-4H-(1,3)thiazeto(3,2-a)quinoline-3-carboxylic acid. Hydrochloride. M.p. not lower than 300° C. (decompn.). IR$_{max}^{KBr}$ (cm$^{-1}$): 3500, 2700, 1690, 1620, 1500, 1390, 1270, 1115, 800.

6-Fluoro-7-morpholino-4-oxo-4H-(1,3)thiazeto(3,2-a)quinoline-3-carboxylic acid. M.p. 244°–248° C. (decompn.). Diphosphate m.p. 182°–190° C. (decompn.).

6-Fluoro-7-thiomorpholino-4-oxo-4H-(1,3)thiazeto(3,2-a)quinoline-3-carboxylic acid. M.p. 220°–242° C. (decompn.).

7-(4-Allyl-1-piperazinyl)-6-fluoro-1-methyl-4-oxo-4H-(1,3)thiazeto(3,2-a)quinoline-3-carboxylic acid. M.p. 216°–218° C. (decompn.).

7-(4-Ethyl-1-piperazinyl)-6-fluoro-1-methyl-4-oxo-4H-(1,3)thiazeto(3,2-a)quinoline-3-carboxylic acid. Hydrofluoride, m.p. 211°–214° C. (decompn.).

6-Fluoro-7-(4-isopropyl-1-piperazinyl)-1-methyl-4-oxo-4H-(1,3)thiazeto(3,2-a)quinoline-3-carboxylic acid. M.p. 227°–228° C. (decompn.).

6-Fluoro-7-(4-(2-hydroxyethyl)-1-piperazinyl)-1-methyl-4-oxo-4H-(1,3)thiazeto(3,2-a)quinoline-3-carboxylic acid. M.p. 230°–232° C. (decompn.).

7-(3-Aminomethyl-1-pyrrolidinyl)-6-fluoro-1-methyl-4-oxo-4H-(1,3)thiazeto(3,2-a)quinoline-3-carboxylic acid. M.p. 213° C. (decompn.).

6-Fluoro-7-(3-hydroxy-1-pyrrolidinyl)-1-methyl-4-oxo-4H-(1,3)thiazeto(3,2-a)quinoline-3-carboxylic acid. M.p. 253° C. (decompn.). Sulfate, m.p. 206°–208° C. (decompn.).

6-Fluoro-7-(imidazol-1-yl)-1-methyl-4-oxo-4H-(1,3)thiazeto(3,2-a)quinoline-3-carboxylic acid. M.p. 248°–251° C. (decompn.).

6-Fluoro-7-(3-hydroxymethyl-1-pyrrolidinyl)-1-methyl-4-oxo-4H-(1,3)thiazeto(3,2-a)quinoline-3-carboxylic acid. M.p. 268°–270° C. (decompn.).

7-(4-Acetyl-1-piperazinyl)-6-fluoro-1-methyl-4-oxo-4H-(1,3)thiazeto(3,2-a)quinoline-3-carboxylic acid. M.p. 263°–265° C. (decompn.).

6-Fluoro-1-methyl-7-morpholino-4-oxo-4H-(1,3)thiazeto(3,2-a)quinoline-3-carboxylic acid. M.p. 250°–252° C. (decompn.). Sulfate, m.p. 192°–198° C. (decompn.).

6-Fluoro-1-methyl-7-thiomorpholino-4-oxo-4H-(1,3)thiazeto(3,2-a)quinoline-3-carboxylic acid. M.p. 258°–260° C. (decompn.). Sulfate, m.p. 229°–231° C. (decompn.).

6-Fluoro-7-(4-methyl-1-homopiperazinyl)-1-methyl-4-oxo-4H-(1,3)thiazeto(3,2-a)quinoline-3-carboxylic acid. M.p. 158°–164° C. (decompn.).

6-Fluoro-7-(3-hydroxypiperidino)-1-methyl-4-oxo-4H-(1,3)thiazeto(3,2-a)quinoline-3-carboxylic acid. M.p. 255°–257° C. (decompn.).

7-(4-(4-aminobenzyl)-1-piperazinyl)-6-fluoro-1-methyl-4-oxo-4H-(1,3)thiazeto(3,2-a)quinoline-3-carboxylic acid. M.p. 209°–211° C. (decompn.).

6-Fluoro-7-(2-methylimidazol-1-yl)-1-methyl-4-oxo-4H-(1,3)thiazeto(3,2-a)quinoline-3-carboxylic acid. M.p. 282°–284° C. (decompn.).

6-Fluoro-7-(4-hydroxypiperidino)-1-methyl-4-oxo-4H-(1,3)thiazeto(3,2-a)quinoline-3-carboxylic acid. M.p. 266°–268° C. (decompn.).

6-Fluoro-7-piperidino-1-methyl-4-oxo-4H-(1,3)thiazeto(3,2-a)quinoline-3-carboxylic acid. M.p. 246°–248° C. (decompn.).

6-Fluoro-1-methyl-7-(1-pyrrolidinyl)-4-oxo-4H-(1,3)thiazeto(3,2-a)quinoline-3-carboxylic acid. M.p. 275°–277° C. (decompn.).

6-Fluoro-7-(4-(4-methoxyphenyl)-1-piperazinyl)-1-methyl-4-oxo-4H-(1,3)thiazeto(3,2-a)quinoline-3-carboxylic acid. M.p. 258°–260° C. (decompn.).

6-Fluoro-7-(4-phenyl-1-piperazinyl)-1-methyl-4-oxo-4H-(1,3)thiazeto(3,2-a)quinoline-3-carboxylic acid. M.p. 267°–269° C. (decompn.).

6-Fluoro-7-(3-hydroxy-4-hydroxymethyl-1-pyrrolidinyl)-1-methyl-4-oxo-4H-(1,3)thiazeto(3,2-a)quinoline-3-carboxylic acid. M.p. 245°–246° C. (decompn.).

6-Fluoro-7-(3,4-di(2-hydroxyethyl)-1-pyrrolidinyl)-1-methyl-4-oxo-4H-(1,3)thiazeto(3,2-a)quinoline-3-carboxylic acid. M.p. 220°–221° C. (decompn.).

7-(N,N-Dihydroxyethylamino)-6-fluoro-1-methyl-4-oxo-4H-(1,3)thiazeto(3,2-a)quinoline-3-carboxylic acid. M.p. 227°–230° C. (decompn).

6-Fluoro-1-methyl-7-(3-amino-1-pyrrolidinyl)-4-oxo-4H-(1,3)thiazeto(3,2-a)quinoline-3-carboxylic acid. M.p. 222°–230° C. (decompn.). Ethanesulfonate, m.p. 250°–251° C. (decompn.). d-10-Camphorsulfonate, m.p. 238°–240° C. (decompn.).

6-Fluoro-1-methyl-7-(4-methyl-1-piperidino)-4-oxo-4H-(1,3)thiazeto(3,2-a)quinoline-3-carboxylic acid. M.p. 249°–251° C. (decompn.). 7-(3-Dimethylamino-1-pyrrolidinyl)-6-fluoro-1-methyl-4-oxo-4H-(1,3)thiazeto(3,2-a)quinoline-3-carboxylic acid. Hydrochloride, m.p. 275°–276° C. (decompn.).

6-Fluoro-1-methyl-7-(3-oxo-1-piperazinyl)-4-oxo-4H-(1,3)thiazeto(3,2-a)quinoline-3-carboxylic acid. M.p. 254°–256° C. (decompn.). Sulfate, m.p. 198°–200° C. (decompn.).

6-Fluoro-1-methyl-7-(3-methylamino-1-pyrrolidinyl)-4-oxo-4H-(1,3)thiazeto(3,2-a)quinoline-3-carboxylic acid. Hydrochloride, m.p. 213°–216° C. (decompn.).

6-Fluoro-1-methyl-7-(4-methyl-1-piperazinyl)-8-nitro-4-oxo-4H-(1,3)thiazeto(3,2-a)quinoline-3-carboxylic acid. Nitrate, m.p. not lower than 300° C. (decompn.). IR$_{max}^{KBr}$ (cm$^{-1}$): 3400, 1700, 1620, 1595, 1530, 1480, 1450, 1380, 1270, 1125, 1070, 970, 800.

6-Fluoro-1-methyl-7-(4-methyl-3-oxo-1-piperazinyl)-4-oxo-4H-(1,3)thiazeto(3,2-a)quinoline-3-carboxylic acid. M.p. 254°–255° C. (decompn.).

8-Amino-6-fluoro-1-methyl-7-(4-methyl-1-piperazinyl)-4-oxo-4H-(1,3)thiazeto(3,2-a)quinoline-3-carboxylic acid. M.p. 240° C. (decompn.).

Ethyl 8-chloro-6-fluoro-1-methyl-7-(4-methyl-1-piperazinyl)-4-oxo-4H-(1,3)thiazeto(3,2-a)quinoline-3-carboxylate. M.p. 196°–197° C.

Ethyl 6-fluoro-1-methyl-7-(4-methyl-1-piperazinyl)-8-nitro-4-oxo-4H-(1,3)thiazeto(3,2-a)quinoline-3-carboxylate. M.p. 185°–188° C. (decompn.).

Ethyl 6-fluoro-1-methyl-7-(4-methyl-1-piperazinyl)-4-oxo-4H-(1,3)thiazeto(3,2-a)quinoline-3-carboxylate. M.p. 223°–225° C.

Ethyl 8-bromo-6-fluoro-1-methyl-7-(4-methyl-1-piperazinyl)-4-oxo-4H-(1,3)thiazeto(3,2-a)quinoline-3-carboxylate. M.p. 191°–192° C. (decompn.). 8-Chloro-6-fluoro-1-methyl-7-(4-methyl-1-piperazinyl)-4-oxo-4H-(1,3)thiazeto(3,2-a)quinoline-3-carboxylic acid. M.p. 189°–190° C. (decompn.).

8-Bromo-6-fluoro-1-methyl-7-(4-methyl-1-piperazinyl)-4-oxo-4H-(1,3)thiazeto(3,2-a)quinoline-3-carboxylic acid. M.p. 198°–200° C. (decompn.).

Ethyl 8-amino-6-fluoro-1-methyl-7-(4-methyl-1-piperazinyl)-4-oxo-4H-(1,3)thiazeto(3,2-a)quinoline-3-carboxylate. M.p. 200°–205° C. (decompn.).

Ethyl 6-fluoro-7-(4-methyl-1-piperazinyl)-4-oxo-4H-(1,3)thiazeto(3,2-a)quinoline-3-carboxylate. M.p. 260°–265° C. (decompn.).

Ethyl 8-acetamido-6-fluoro-1-methyl-7-(4-methyl-1-piperazinyl)-4-oxo-4H-(1,3)thiazeto(3,2-a)quinoline-3-carboxylate. M.p. 192°–195° C. (decompn.).

Ethyl 8-diacetylamino-6-fluoro-1-methyl-7-(4-methyl-1-piperazinyl)-4-oxo-4H-(1,3)thiazeto(3,2-a)quinoline-3-carboxylate. M.p. 212°–214° C. (decompn.).

6-Fluoro-1-methyl-4-oxo-7-(1-piperazinyl)-4H-(1,3)thiazeto(3,2-a)quinoline-3-carboxylic acid. M.p. 215°–218° C. (decompn.). ½ Sulfate, m.p. 285° C. (decompn.); hydrochloride, m.p. 295°–300° C. (decompn.); methanesulfonate, m.p. 236°–239° C. (decompn.); p-toluenesulfonate, m.p. 196°–200° C. (decompn.); maleate, m.p. 225°–227° C. (decompn.).

Ethyl 7-dimethylamino-6-fluoro-1-methyl-4-oxo-4H-(1,3)thiazeto(3,2-a)quinoline-3-carboxylate. M.p. 194° C.

Ethyl 6-fluoro-1-methyl-7-(3-methyl-1-piperazinyl)-4-oxo-4H-(1,3)thiazeto(3,2-a)quinoline-3-carboxylate. M.p. 133°–135° C.

Ethyl 6-fluoro-7-(4-isopropyl-1-piperazinyl)-1-methyl-4-oxo-4H-(1,3)thiazeto(3,2-a)quinoline-3-carboxylate. M.p. 230°–231° C.

Ethyl 1-ethyl-6-fluoro-7-(4-methyl-1-piperazinyl)-4-oxo-4H-(1,3)thiazeto(3,2-a)quinoline-3-carboxylate. M.p. 211°–212° C.

Ethyl 6-fluoro-7-(3-methyl-1-piperazinyl)-4-oxo-4H-(1,3)thiazeto(3,2-a)quinoline-3-carboxylate. M.p. not lower than 300° C. (decompn.). IR$_{max}^{KBr}$ (cm$^{-1}$): 3400, 2950, 1705, 1625, 1595, 1500, 1370, 1320, 1250, 1155, 1050, 895, 850, 795.

Ethyl 7-(3,4-dimethyl-1-piperazinyl)-6-fluoro-4-oxo-4H-(1,3)thiazeto(3,2-a)quinoline-3-carboxylate. M.p. 262° C. (decompn.).

Ethyl 6-fluoro-1-methyl-7-morpholino-4-oxo-4H-(1,3)thiazeto(3,2-a)quinoline-3-carboxylate. M.p. 257°–258° C. (decompn.).

Ethyl 7-(3,4-dimethyl-1-piperazinyl)-6-fluoro-1-methyl-4-oxo-4H-(1,3)thiazeto(3,2-a)quinoline-3-carboxylate. M.p. 204°–206° C.

Ethyl 6-fluoro-7-(3-hydroxymethyl-1-pyrrolidinyl)-1-methyl-4-oxo-4H-(1,3)thiazeto(3,2-a)quinoline-3-carboxylate. M.p. 230°–233° C. (decompn.).

Ethyl 6-fluoro-4-oxo-7-(1-piperazinyl)-4H-(1,3)thiazeto(3,2-a)quinoline-3-carboxylate. M.p. not lower than 300° C. (decompn.). IR$_{max}^{KBr}$ (cm$^{-1}$): 3400, 3260, 1705, 1625, 1595, 1540, 1500, 1370, 1325, 1250, 1160, 1090, 1040, 795.

Ethyl 6-fluoro-1-methyl-7-(4-methyl-3-oxo-1-piperazinyl)-4-oxo-4H-(1,3)thiazeto(3,2-a)quinoline-3-carboxylate. M.p. 195°–198° C.

Ethyl 6-fluoro-7-(4-methyl-1-piperazinyl)-4-oxo-1-phenyl-4H-(1,3)thiazeto(3,2-a)quinoline-3-carboxylate. M.p. 208°–209° C.

Ethyl 6-fluoro-4-oxo-1-phenyl-7-(1-piperazinyl)-4H-(1,3)thiazeto(3,2-a)quinoline-3-carboxylate. M.p. 189°–191° C. (decompn.).

Ethyl 6-fluoro-7-(3-methyl-1-piperazinyl)-4-oxo-1-phenyl-4H-(1,3)thiazeto(3,2-a)quinoline-3-carboxylate. M.p. 153° C.

Ethyl 7-(3,4-dimethyl-1-piperazinyl)-6-fluoro-4-oxo-1-phenyl-4H-(1,3)thiazeto(3,2-a)quinoline-3-carboxylate. M.p. 165° C.

Isopropyl 6-fluoro-1-methyl-4-oxo-7-(1-piperazinyl)-4H-(1,3)thiazeto(3,2-a)quinoline-3-carboxylate. M.p. 220° C. (decompn.).

7-(3,4-Dimethyl-1-piperazinyl)-6-fluoro-1-methyl-4-oxo-4H-(1,3)thiazeto(3,2-a)quinoline-3-carboxylic acid. M.p. 198°–201° C. (decompn.). Formate, m.p. 220° C. (decompn.).

Methyl 6-fluoro-1-methyl-4-oxo-7-(1-piperazinyl)-4H-(1,3)thiazeto(3,2-a)quinoline-3-carboxylate. M.p. 208° C. (decompn.).

6-Chloro-4-oxo-7-(1-piperazinyl)-4H-(1,3)thiazeto(3,2-a)quinoline-3-carboxylic acid. M.p. 235°–240° C. (decompn.).

6-Chloro-7-(4-methyl-1-piperazinyl)-4-oxo-4H-(1,3)thiazeto(3,2-a)quinoline-3-carboxylic acid. M.p. 220°–230° C. (decompn.).

6-Chloro-1-methyl-7-(4-methyl-1-piperazinyl)-4-oxo-4H-(1,3)thiazeto(3,2-a)quinoline-3-carboxylic acid. M.p. 257°–259° C. (decompn.). Hydrochloride, m.p. 250°–255° C. (decompn.). Sulfate, m.p. 225°–230° C. (decompn.).

Ethyl 7-(4-acetonyl-3-methyl-1-piperazinyl)-6-fluoro-1-methyl-4-oxo-4H-(1,3)thiazeto(3,2-a)quinoline-3-carboxylate. M.p. 190°–192° C.

Methyl 7-(3,4-dimethyl-1-piperazinyl)-6-fluoro-1-methyl-4-oxo-4H-(1,3)thiazeto(3,2-a)quinoline-3-carboxylate. M.p. 199°–204° C. (decompn.).

Isopropyl 7-(3,4-dimethyl-1-piperazinyl)-6-fluoro-1-methyl-4-oxo-4H-(1,3)thiazeto(3,2-a)quinoline-3-carboxylate. M.p. 194°–197° C. (decompn.).

Ethyl 7-(4-acetonyl-1-piperazinyl)-6-fluoro-1-phenyl-4-oxo-4H-(1,3)thiazeto(3,2-a)quinoline-3-carboxylate. M.p. 190°–191° C. (decompn.).

7-(4-Acetonyl-1-piperazinyl)-6-fluoro-1-methyl-4-oxo-4H-(1,3)thiazeto(3,2-a)quinoline-3-carboxylic acid. M.p. 208°–209° C. (decompn.). Hydrochloride, m.p. 255°–257° C. (decompn.); methanesulfonate, m.p. 215°–218° C. (decompn.); maleate, m.p. 156°–158° C. (decompn.); p-toluenesulfonate, m.p. 245°–248° C. (decompn.); sodium salt, m.p. >300° C. (decompn.).

Ethyl 7-(4-acetonyl-1-piperazinyl)-6-fluoro-4-oxo-4H-(1,3)thiazeto(3,2-a)quinoline-3-carboxylate. M.p. 248°–250° C. (decompn.). 6-Fluoro-1-methyl-7-(3-methyl-1-piperazinyl)-4-oxo-4H-(1,3)thiazeto(3,2-a)quinoline-3-carboxylic acid. M.p. 170°–172° C. (decompn.).

Ethyl 6-fluoro-8-methoxy-1-methyl-7-(4-methyl-1-piperazinyl)-4-oxo-4H-(1,3)thiazeto(3,2-a)quinoline-3-carboxylate. M.p. 213° C. (decompn.).

Glycerol 6-fluoro-1-methyl-7-(1-piperazinyl)-4-oxo-4H-(1,3)thiazeto(3,2-a)quinoline-3-carboxylate. M.p. 155°–160° C.

n-Butyl 6-fluoro-1-methyl-7-(1-piperazinyl)-4-oxo-4H-(1,3)thiazeto(3,2-a)quinoline-3-carboxylate. M.p. 212°–213° C. (decompn.).

Ethyl 6-fluoro-1-methyl-7-(4-(3-methyl-2-oxobutyl)-1-piperazinyl)-4-oxo-4H-(1,3)thiazeto(3,2-a)quinoline-3-carboxylate. M.p. 183° C.

Ethyl 1-(4-chlorophenyl)-6-fluoro-7-(4-methyl-1-piperazinyl)-4-oxo-4H-(1,3)thiazeto(3,2-a)quinoline-3-carboxylate. M.p. 142°-143° C.

3-Hydroxypropyl 6-fluoro-1-methyl-7-(1-piperazinyl)-4-oxo-4H-(1,3)thiazeto(3,2-a)quinoline-3-carboxylate. M.p. 208°-209° C. (decompn.).

Methoxyethyl 6-fluoro-1-methyl-7-(1-piperazinyl)-4-oxo-4H-(1,3)thiazeto(3,2-a)quinoline-3-carboxylate. M.p. 198°-201° C. (decompn.).

Hydroxyethyl 6-fluoro-1-methyl-7-(1-piperazinyl)-4-oxo-4H-(1,3)thiazeto(3,2-a)quinoline-3-carboxylate. M.p. 164°-168° C. (decompn.).

Ethyl 6-fluoro-1-methyl-4-oxo-7-(4-(2-oxo-2-phenylethyl)-1-piperazinyl)-4H-(1,3)thiazeto(3,2-a)quinoline-3-carboxylate. M.p. 203°-205° C. (decompn.).

Ethyl 7-(4-(3,3-dimethyl-2-oxobutyl)-1-piperazinyl)-6-fluoro-1-methyl-4-oxo-4H-(1,3)thiazeto(3,2-a)quinoline-3-carboxylate. M.p. 180°-182° C. (decompn.).

Ethyl 6-fluror-1-methyl-4-oxo-7-(4-(3-oxobutyl)-1-piperazinyl)-4H-(1,3)thiazeto(3,2-a)quinoline-3-carboxylate. M.p. 169°-171° C. (decompn.).

Ethyl 6-fluoro-1-methyl-4-oxo-7-(4-trifluoroacetyl-1-piperazinyl)-4H-(1,3)thiazeto(3,2-a)quinoline-3-carboxylate. M.p. 241°-242° C. (decompn.).

Hydroxyethyl 7-(4-ethyl-1-piperazinyl)-6-fluoro-1-methyl-4-oxo-4H-(1,3)thiazeto(3,2-a)quinoline-3-carboxylate. M.p. 159°-162° C. (decompn.).

Ethyl 7-(4-ethyl-1-piperazinyl)-6-fluoro-1-methyl-4-oxo-4H-(1,3)thiazeto(3,2-a)quinoline-3-carboxylate. M.p. 236°-238° C. (decompn.).

Ethyl 6-fluoro-7-(4-(2-methoxyethyl)-1-piperazinyl)-1-methyl-4-oxo-4H-(1,3)thiazeto(3,2-a)quinoline-3-carboxylate. M.p. 188°-189° C.

Ethyl 7-(4-carboethoxymethyl-1-piperazinyl)-6-fluoro-1-methyl-4-oxo-4H-(1,3)thiazeto(3,2-a)quinoline-3-carboxylate. M.p. 205°-207° C. (decompn.).

Ethyl 6-fluoro-7-(4-hydroxyethyl-1-piperazinyl)-1-methyl-4-oxo-4H-(1,3)thiazeto(3,2-a)quinoline-3-carboxylate. M.p. 215°-216° C. (decompn.).

Ethyl 7-(4-cyanomethyl-1-piperazinyl)-6-fluoro-1-methyl-4-oxo-4H-(1,3)thiazeto(3,2-a)quinoline-3-carboxylate. M.p. 252°-253° C. (decompn.).

Ethyl 6-fluoro-1-methyl-7-(4-(2-propynyl)-1-piperazinyl)-4-oxo-4H-(1,3)thiazeto(3,2-a)quinoline-3-carboxylate. M.p. 209°-210° C. (decompn.).

Ethyl 6-fluoro-7-morpholino-4-oxo-1-phenyl-4H-(1,3)thiazeto(3,2-a)quinoline-3-carboxylate. M.p. 211° C.

Ethyl 6-fluoro-7-(4-(2-hydroxyethoxyethyl)-1-piperazinyl)-1-methyl-4-oxo-4H-(1,3)thiazeto(3,2-a)quinoline-3-carboxylate. M.p. 196°-198° C.

6-Fluoro-1-(4-fluorophenyl)-4-oxo-7-(1-piperazinyl)-4H-(1,3)thiazeto(3,2-a)quinoline-3-carboxylic acid. M.p. 298°-304° C. (decompn.). Ethyl ester, m.p. 192° C. (decompn.).

1-(2,4-Difluorophenyl)-6-fluoro-4-oxo-7-(1-piperazinyl)-4H-(1,3)thiazeto(3,2-a)quinoline-3-carboxylic acid. M.p. >300° C. (decompn.). Ethyl ester, m.p. 180° C. (decompn.).

1-(2,5-Difluorophenyl)-6-fluoro-4-oxo-7-(1-piperazinyl)-4H-(1,3)thiazeto(3,2-a)quinoline-3-carboxylic acid. M.p. 280°-284° C. (decompn.).

6-Fluoro-7-(4-methyl-1-piperazinyl)-4-oxo-1-phenyl-4H-(1,3)thiazeto(3,2-a)quinoline-3-carboxylic acid. M.p. 216°-217° C. (decompn.). Hydrochloride, m.p. 270° C. (decompn.); methanesulfonate, m.p. 205°-210° C. (decompn.); p-toluenesulfonate, m.p. 160°-166° C.; maleate, m.p. 180°-182° C. (decompn.); sodium salt, m.p. 290°-300° C. (decompn.).

6-Fluoro-4-oxo-1-phenyl-7-(1-piperazinyl)-4H-(1,3)thiazeto(3,2-a)quinoline-3-carboxylic acid. M.p. 210°-230° C. (decompn.); hydrochloride, m.p. 220° C. (decompn.); p-toluenesulfonate, m.p. 200°-205° C. (decompn.); maleate, m.p. 210° C. (decompn.).

Pivaloyloxymethyl 6-fluoro-7-(4-methyl-1-piperazinyl)-4-oxo-1-phenyl-4H-(1,3)thiazeto(3,2-a)quinoline-3-carboxylate. M.p. 169°-172° C.

Pivaloyloxymethyl 7-(4-acetonyl-1-piperazinyl)-6-fluoro-1-methyl-4-oxo-4H-(1,3)thiazeto(3,2-a)quinoline-3-carboxylate. M.p. 132°-135° C.

6-Fluoro-8-methoxy-1-methyl-7-(4-methyl-1-piperazinyl)-4-oxo-4H-(1,3)thiazeto(3,2-a)quinoline-3-carboxylic acid. M.p. 220° C. (decompn.).

6-Fluoro-8-methoxy-7-(4-methyl-1-piperazinyl)-4-oxo-1-phenyl-4H-(1,3)thiazeto(3,2-a)quinoline-3-carboxylic acid. M.p. 176°-177° C. Ethyl ester, m.p. 96°-98° C. (decompn.).

Ethyl 6-fluoro-8-methoxy-7-(4-methyl-1-piperazinyl)-4-oxo-4H-(1,3)thiazeto(3,2-a)quinoline-3-carboxylate. M.p. 219° C. (decompn.).

1-(2,4-Difluorophenyl)-6-fluoro-7-(4-methyl-1-piperazinyl)-4-oxo-4H-(1,3)thiazeto(3,2-a)quinoline-3-carboxylic acid. M.p. 209°-211° C. (decompn.). Ethyl ester, m.p. 212°-214° C.

1-(2,5-Difluorophenyl)-6-fluoro-7-(4-methyl-1-piperazinyl)-4-oxo-4H-(1,3)thiazeto(3,2-a)quinoline-3-carboxylic acid. M.p. 213°-215° C. (decompn.). Ethyl ester, m.p. 218°-220° C.

1-(2,6-Difluorophenyl)-6-fluoro-7-(4-methyl-1-piperazinyl)-4-oxo-4H-(1,3)thiazeto(3,2-a)quinoline-3-carboxylic acid. M.p. 229°-232° C. (decompn.). Ethyl ester, m.p. 144°-147° C. (decompn.).

1-(3,4-Difluorophenyl)-6-fluoro-7-(4-methyl-1-piperazinyl)-4-oxo-4H-(1,3)thiazeto(3,2-a)quinoline-3-carboxylate. M.p. 277°-280° C. (decompn.). Ethyl ester, m.p. 170°-173° C.

6-Fluoro-1-(4-fluorophenyl)-7-(4-methyl-1-piperazinyl)-4-oxo-4H-(1,3)thiazeto(3,2-a)quinoline-3-carboxylic acid. M.p. 208°-215° C. (decompn.). Ethyl ester, m.p. 121°-122° C.

6-Fluoro-1-(3-fluorophenyl)-7-(4-methyl-1-piperazinyl)-4-oxo-4H-(1,3)thiazeto(3,2-a)quinoline-3-carboxylic acid. M.p. 222°-225° C. (decompn.). Ethyl ester, m.p. 180°-183° C.

6-Fluoro-1-(2-fluorophenyl)-7-(4-methyl-1-piperazinyl)-4-oxo-4H-(1,3)thiazeto(3,2-a)quinoline-3-carboxylic acid. M.p. 203°-205° C. (decompn.). Ethyl ester, m.p. 198°-201° C.

6-Fluoro-1-(4-methylphenyl)-7-(4-methyl-1-piperazinyl)-4-oxo-4H-(1,3)thiazeto(3,2-a)quinoline-3-carboxylic acid. M.p. 191°-193° C. (decompn.). Ethyl ester, m.p. 156°-160° C.

6-Fluoro-1-(2-methylphenyl)-7-(4-methyl-1-piperazinyl)-4-oxo-4H-(1,3)thiazeto(3,2-a)quinoline-3-carboxylic acid. M.p. 185°-187° C. (decompn.). Ethyl ester, m.p. 162°-165° C.

Ethyl 6-fluoro-7-(4-methyl-1-piperazinyl)-1-(4-nitrophenyl)-4-oxo-4H-(1,3)thiazeto(3,2-a)quinoline-3-carboxylate. M.p. 228°-231° C. (decompn.).

6-Fluoro-7-(4-methyl-1-piperazinyl)-1-(4-trifluorophenyl)-4-oxo-4H-(1,3)thiazeto(3,2-a)quinoline-3-carboxylic acid. M.p. 239°-242° C. (decompn.). Ethyl ester, m.p. 200°-203° C.

6-Fluoro-7-(4-methyl-1-piperazinyl)-1-(3-trifluorophenyl)-4-oxo-4H-(1,3)thiazeto(3,2-a)quinoline-3-carboxylic acid. M.p. 223°–226° C. (decompn.). Ethyl ester, m.p. 206°–209° C.

The following experiments were conducted to show the antibacterial activity of representative compounds of the present invention.

1. Measurement of minimum inhibitory concentration (MIC).

Test method: The MIC was measured by an agar plate dilution method in accordance with a standard method of Japan Chemotherapeutic Society (cf. Nippon Kagaku Ryoho Gakkaishi, 29(1), 76–79, 1981). Thus, the organisms incubated at 37° C. for 18 hours using sensitivity test broth (Nissei) was diluted to $10^6$ CFU/ml using the same broth. This was inoculated, using a microplanter, to a drug-containing sensitivity test agar (Nissei), cultured at 37° C. for 18 hours, and the MIC was measured. As a control, enoxacin and ofloxacin were used in Tests 1 and 2, respectively. The result is given in Table 1. The compounds (1) to (14) were tested and exhibited very strong antibacterial activity against both Gram-positive and gram negative bacteria including Pseudomonas aeruginosa.

(1): 6-Fluoro-7-(4-methyl-1-piperazinyl)-4-oxo-4H-(1,3)thiazeto(3,2-a)quinoline-3-carboxylic acid;

(2): 6-Fluoro-1-methyl-7-(4-methyl-1-piperazinyl)-4-oxo-4H-(1,3)thiazeto(3,2-a)quinoline-3-carboxylic acid;

(3): 6-Fluoro-7-morpholino-4-oxo-4H-(1,3)thiazeto(3,2-a)quinoline-3-carboxylic acid;

(4): 7-(4-Allyl-1-piperazinyl)-6-fluoro-1-methyl-4-oxo-4H-(1,3)thiazeto(3,2-a)quinoline-3-carboxylic acid;

(5): 6-Fluoro-1-methyl-7-(4-methyl-1-piperazinyl)-4-oxo-4H-(1,3)thiazeto(3,2-a)quinoline-3-carboxylic acid sulfate;

(6): 6-Fluoro-1-methyl-7-thiomorpholino-4-oxo-4H-(1,3)thiazeto(3,2-a)quinoline-3-carboxylic acid sulfate;

(7): 6-Chloro-1-methyl-4-oxo-7-(1-piperazinyl)-4H-(1,3)thiazeto(3,2-a)quinoline-3-carboxylic acid;

(8): 6-Fluoro-1-methyl-7-(3-amino-1-pyrrolidinyl)-4-oxo-4H-(1,3)thiazeto(3,2-a)quinoline-3-carboxylic acid ethanesulfonate;

(9): 8-Amino-6-fluoro-1-methyl-7-(4-methyl-1-piperazinyl)-4-oxo-4H-(1,3)thiazeto(3,2-a)quinoline-3-carboxylic acid; and

TABLE 1

| Strains Used | Enoxacin | (1) | (2) | (3) | (4) | (5) | (6) | (7) | (8) | (9) | (10) |
|---|---|---|---|---|---|---|---|---|---|---|---|
| ① S. aureus 209 - P JC | 0.78 | 0.05 | 0.1 | 0.025 | 0.05 | 0.1 | 0.05 | 0.1 | 0.025 | 0.39 | 0.05 |
| ② S. aureus Smith | 0.78 | 0.05 | 0.05 | ≦0.0063 | 0.05 | 0.05 | ≦0.0063 | 0.2 | 0.05 | 0.2 | ≦0.0063 |
| ③ M. luteus ATCC 9341 | 25 | 12.5 | 1.56 | 12.5 | 1.56 | 1.56 | 1.56 | 1.56 | 0.2 | 50 | 0.39 |
| ④ B. subtilis ATCC 6633 | 0.2 | 0.025 | 0.025 | ≦0.0063 | 0.025 | 0.025 | ≦0.0063 | 0.2 | 0.05 | 0.2 | ≦0.0063 |
| ⑤ E. coli NIHJ JC-2 | 0.2 | 0.0125 | 0.025 | 0.1 | 0.05 | 0.025 | 0.2 | 0.05 | 0.05 | 0.1 | 0.2 |
| ⑥ E. coli KC-14 | 0.1 | ≦0.0063 | ≦0.0063 | 0.025 | 0.025 | ≦0.0063 | 0.05 | 0.025 | ≦0.0063 | 0.05 | 0.05 |
| ⑦ K. pneumoniae K-1966 | 0.2 | 0.025 | 0.025 | 0.025 | 0.05 | 0.025 | 0.1 | 0.025 | 0.025 | 0.1 | 0.2 |
| ⑧ E. cloacae No. 1 | 0.1 | 0.025 | 0.025 | 0.39 | 0.1 | 0.025 | 0.39 | 0.05 | 0.025 | 0.2 | 0.39 |
| ⑨ S. marcescens IFO 3736 | 0.39 | 0.05 | 0.05 | 0.2 | 0.2 | 0.05 | 0.78 | 0.1 | 0.1 | 0.39 | 0.56 |
| ⑩ P. vulgaris HX-19 | 0.05 | ≦0.0063 | 0.0125 | ≦0.0063 | 0.0125 | 0.0125 | ≦0.0063 | 0.025 | ≦0.0063 | 0.025 | 0.1 |
| ⑪ S. flexneri | 0.1 | ≦0.0063 | 0.0125 | 0.025 | 0.025 | 0.0125 | 0.1 | 0.0125 | ≦0.0063 | 0.05 | 0.1 |
| ⑫ P. aeruginosa E-2 | 0.78 | 0.39 | 0.39 | 0.78 | 0.78 | 0.39 | 0.78 | 1.56 | 0.1 | 1.56 | 3.13 |
| ⑬ A. calcoaceticus 54 | 1.56 | 0.39 | 0.2 | 0.39 | 0.1 | 0.19 | 0.2 | 3.13 | 0.78 | 0.78 | 0.39 |

| Strains Used | Ofloxacin | (11) | (12) | (13) | (14) |
|---|---|---|---|---|---|
| ① S. aureus 209-P JC | 0.78 | 0.2 | 0.2 | 0.1 | 0.1 |
| ② S. epidermidis | 1.56 | 1.56 | 0.39 | 3.13 | 0.39 |
| ③ M. luteus ATTC 9341 | 3.13 | 3.13 | 1.56 | 1.56 | 0.2 |
| ④ B. subtilis ATCC 6633 | 0.2 | 0.05 | 0.05 | 0.1 | 0.025 |
| ⑤ E. coli NIHJ JC-2 | 0.05 | 0.025 | 0.025 | 0.0125 | 0.05 |
| ⑥ K. pneumoniae K-1966 | 0.1 | 0.025 | 0.0125 | 0.0125 | 0.025 |
| ⑦ S. Marcescens IFO 3736 | 0.39 | 0.05 | 0.39 | 0.05 | 0.2 |
| ⑧ Proteus mirabilis 181 | 0.1 | 0.05 | 0.2 | 0.025 | 0.0125 |
| ⑨ S. flexneri | 0.1 | 0.025 | 0.025 | 0.0125 | 0.0125 |
| ⑩ P. aeruginosa E-2 | 1.56 | 0.2 | 0.39 | 0.2 | 0.39 |

The compounds of the present invention designated as (1) to (14) in the above table 1 are as follows.

(10): 7-(4-(4-Aminobenzyl)-1-piperazinyl)-6-fluoro-1-methyl-4-oxo-4H-(1,3)thiazeto(3,2-a)quinoline-3-carboxylic acid;

(11): 6-Fluoro-4-oxo-1-phenyl-7-(1-piperazinyl)-4H-(1,3)thiazeto(3,2-a)quinoline-3-carboxylic acid;

(12): 6-Fluoro-1-(4-fluorophenyl)-4-oxo-7-(1-piperazinyl)-4H-(1,3)thiazeto(3,2-a)quinoline-3-carboxylic acid;

(13): 6-Fluoro-1-methyl-4-oxo-7-(1-piperazinyl)-4H-(1,3)thiazeto(3,2-a)quinoline-3-carboxylic acid; and (14): 6-Fluoro-8-methoxy-1-methyl-7-(4-methyl-1-piperazinyl)-4-oxo-4H-(1,3)thiazeto(3,2-a)quinoline-3-carboxylic acid.

The numbers of the inoculated bacteria were $10^6$ in all cases and the unit of the MIC was micrograms/ml.

2. Therapeutic Effect on Infection in Mice.

Test Method: *Escherichia coli* KC-14 and *Psudomonas aeruginosa* E-2 were suspended in 4% mucin and 0.25 ml of it was inoculated into peritoneal cavity of ddY-strain male mice (body weight about 20 g; 4 weeks age; 10 mice per group). The numbers of the inoculated bacteria were $5.1 \times 10^4$ CFU/mouse and $7.5 \times 10^4$ CFU/mouse for *E. coli* and *P. aeruginosa*, respectively. The drug was administered orally once 2 hours after the infection of the bacteria and, out of the survival rate after one week, the $ED_{50}$ values were calculated by a Behrens-Karber method. As controls, ofloxacin and enoxacin were used. The result is given in Table 2.

TABLE 2

| Compound | $ED_{50}$ (mg/kg) | |
|---|---|---|
| | (1) | (2) |
| Ofloxacin | 0.8 | 16.0 |
| Enoxacin | 1.8 | 13.1 |
| (1) | 0.5 | 4.2 |
| (2) | 0.5 | 4.0 |
| (3) | 0.6 | 5.0 |
| (4) | 0.5 | 4.4 |
| (5) | 0.4 | 4.5 |
| (6) | 0.6 | 5.0 |
| (7) | 0.5 | 4.0 |

Bacteria used for calculating $ED_{50}$ were *E. coli* KC-14 for (1) and *P. aeruginosa* E-2 for (2). The compounds (1) to (7) of the present invention designated in Table 2 are as follows.

(1): 6-Fluoro-1-methyl-7-(4-methyl-1-piperazinyl)-4-oxo-4H-(1,3)thiazeto(3,2-a)quinoline-3-carboxylic acid;

(2): Ethyl 6-fluoro-1-methyl-7-(4-methyl-1-piperazinyl)-4-oxo-4H-(1,3)thiazeto(3,2-a)quinoline-3-carboxylate;

(3): Ethyl 7-(3,4-dimethyl-1-piperazinyl)-6-fluoro-1-methyl-4-oxo-4H-(1,3)thiazeto(3,2-a)quinoline-3-carboxylate;

(4): Ethyl 6-fluoro-7-(4-methyl-1-piperazinyl)-4-oxo-1-phenyl-4H-(1,3)thiazeto(3,2-a)quinoline-3-carboxylate;

(5): Ethyl 7-(4-acetonyl-1-piperazinyl)-6-fluoro-1-methyl-4-oxo-4H-(1,3)thiazeto(3,2-a)quinoline-3-carboxylate;

(6): 7-(4-Acetonyl-1-piperazinyl)-6-fluoro-1-methyl-4-oxo-4H-(1,3)thiazeto(3,2-a)quinoline-3-carboxylic acid; and (7): 6-Fluoro-1-methyl-7-(4-methyl-1-piperazinyl)-4-oxo-4H-(1,3)thiazeto(3,2-a)quinoline-3-carboxylic acid sulfate.

The compounds of the present invention showed a strong therapeutic effect to infectious diseases to mice. They especially showed stronger activity to *P. aeruginosa* than enoxacin which has been said to exhibit strong action thereto.

3. Acute Toxicity:

The result of oral administration to ddY-strain male mice (7 weeks age; body weight ca. 35 g; 3 mice per group) for 2 weeks was given. All of the present invention compounds tested showed low toxicity. For instance, $LD_{50}$ values of the following compounds were not lower than 3 g/kg at all times. Thus, 6-fluoro-1-methyl-4-oxo-7-(1-piperazinyl)-4H-(1,3)thiazeto(3,2-a)quinoline-3-carboxylic acid; ethyl 7-(3,4-dimethyl-1-piperazinyl)-6-fluoro-1-methyl-4-oxo-4H-(1,3)thiazeto(3,2-a)quinoline-3-carboxylate; ethyl 7-(4-acetonyl-1-piperazinyl)-6-fluoro-1-methyl-4-oxo-4H-(1,3)thiazeto(3,2-a)quinoline-3-carboxylate; and 6-fluoro-1-methyl-7-(4-methyl-1-piperazinyl)-4-oxo-4H-(1,3)thiazeto(3,2-a)quinoline-3-carboxylic acid.

It is quite apparent from the afore-mentioned facts that the compounds of the present invention are effective in much less doses than those of the conventional antibacterials to not only *P. aeruginosa* but also both Gram-positive and negative bacteria and exhibit antibacterial spectra of wide range.

Many of the conventional pharmaceuticals are in free carboxylic acid type and, in general, their bioavailability is not satisfactory. Accordingly, it is often observed that they do not show so much therapeutic effect to infectious diseases as expected from their antibacterial activity in vitro.

Both carboxylic acid type and ester type of the compounds of the present invention showed therapeutic effect to infectious diseases in the test in vivo. Compounds of the ester type exhibited especially good absorbability after oral administration, maintained high blood levels for long time, and showed sufficient therapeutic effect.

In addition, the toxicity of the compounds of the present invention are quite low. Accordingly, the compounds of the present invention can be safely used to mammalian animals including human being as a therapeutic agent for both systemic diseases and local diseases such as, for example, infectious diseases in urinary tract and bilary tract.

The embodiments of the invention in which an exclusive property or privilege is claimed are as follows:

1. A compound of the formula I

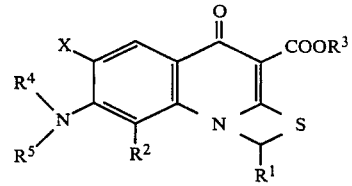

[I]

or a pharmaceutically acceptable salt thereof wherein $R^1$ is hydrogen, straight or branched chain alkyl of 1 to 6 carbon atoms or phenyl unsubstituted or substituted by straight or branched chain alkyl of 1 to 6 carbon atoms, straight or branched chain alkoxy of 1 to 4 carbon atoms, hydroxy, halogen, trifluoromethyl or nitro; $R^2$ is hydrogen, straight or branched chain alkyl of 1 to 6 carbon atoms, straight or branched chain alkoxy of 1 to 4 carbon atoms, hydroxy, halogen, nitro or amino unsubstituted or substituted by acyl of 2 to 6 carbon atoms in the acyl moiety; $R^3$ is is hydrogen or straight or branched chain alkyl of 1 to 6 carbon atoms unsubstituted or substituted by hydroxy, acyloxy of 2 to 6 carbon atoms or straight or branched chain alkoxy of 1 to 4 carbon atoms; $R^4$ and $R^5$ together with the nitrogen atom to which they are attached form a piperazinyl ring unsubstituted or substituted by 1 to 3 substituents selected from the group consisting of straight or branched chain alkyl of 1 to 6 carbon atoms, straight or branched chain alkenyl of 2 to 6 carbon atoms, straight or branched chain alkynyl of 2 to 6 carbon atoms, aryl of 6 to 12 carbon atoms, aralkyl of 7 to 12 carbon atoms, hydroxyalkyl wherein the alkyl moiety is straight or branched chain of 1 to 6 carbon atoms, alkoxyalkyl of 2 to 6 carbon atoms or said alkoxyalkyl of 2 to 6 carbon atoms substituted by hydroxyl, aminoalkyl wherein the alkyl moiety is straight or branched chain of 1 to 6 carbon atoms, cyanoalkyl wherein the alkyl moiety is straight or branched chain of 1 to 6, carboalkoxyalkyl wherein the alkoxy moiety is straight or branched chain of 1 to 4 carbon atoms and the alkyl moiety is straight or branched chain of 1 to 6 carbon atoms, acylalkyl wherein each of the acyl moieties and the alkyl moiety is straight or branched chain of 1 to 6 carbon atoms, acyl of 1 to 6 carbon atoms, hydroxy, oxo, amino, alkylamino wherein the alkyl moiety is straight or branched chain of 1 to 6 carbon atoms or dialkylamino wherein each alkly moiety is straight or branched chain of 1 to 6 carbon atoms; and X is halogen.

2. The compound according to claim 1 wherein the piperazino ring is unsubstituted or substituted by 1 to 3 substituents selected from the group consisting of straight or branched chain alkyl of 1 to 6 carbon atoms, straight or branched chain alkenyl of 2 to 6 carbon atoms, straight or branched chain alkynyl of 2 to 6 carbon atoms, phenyl, alpha-naphthyl, beta-naphthyl, biphenyl, benzyl, phenethyl, phenylpropyl, naphthylmethyl, hydroxyalkyl of 1 to 4 carbon atoms in the alkyl moiety, alkoxyalkyl of 2 to 6 carbon atoms unsubstituted or substituted by hydroxyl, aminoalkyl of 1 to 4 carbon atoms in the alkyl moiety, cyanoalkyl of 1 to 4 carbon atoms in the alkyl moiety, carboalkoxyalkyl of 1 to 4 carbon atoms in each of the alkoxy and alkyl moieties, acylalkyl of 3 to 10 carbon atoms, acyl of 1 to 6 carbon atoms, hydroxy, oxo, amino and mono- or di-alkylamino of 1 to 4 carbon atoms in each alkyl moiety.

3. The compound according to claim 1 wherein $R^1$ is hydrogen, alkyl of 1 to 6 carbon atoms or phenyl; $R^2$ is hydrogen, alkoxy of 1 to 4 carbon atoms or hydroxy; $R^3$ is hydrogen or alkyl of 1 to 6 carbon atoms; and X is fluorine or chlorine.

4. The compound according to claim 1, wherein said piperazine is unsubstituted or substituted by alkyl of from 1 to 4 carbon atoms.

5. The compound according to claim 1, which is 7-(4-acetonyl-1-piperazinyl)-6-fluoro-1-methyl-4-oxo-4H-(1,3)-thiazeto(3,2-a)quinoline-3-carboxylic acid or a pharmaceutically acceptable salt thereof.

6. The compound according to claim 1, which is 6-fluoro-1-methyl-4-oxo-7-(1-piperazinyl)-4H(1,3)-thiazeto-(3,2-a)-quinoline-3-carboxylic acid or a pharmaceutically acceptable salt thereof.

7. The compound according to claim 1, which is ethyl 6-fluoro-1-methyl-4-oxo-7-(1-piperazinyl)-4H-(1,3)-thiazeto-(3,2-a)quinoline-3-carboxylate or a pharmaceutically acceptable salt thereof.

8. The compound according to claim 1, which is ethyl 7-(4-acetonyl-1-piperazinyl)-6-fluoro-1-methyl-4-oxo-4H(1,3)-thiazeto(3,2-a)quinoline-3-carboxylate or a pharmaceutically acceptable salt thereof.

9. The compound according to claim 1, which is 6-fluoro-4-oxo-1-phenyl-7-(1-piperazinyl)-4H-(1,3)thiazeto-(3,2-a)-quinoline-3-carboxylic acid or a pharmaceutically acceptable salt thereof.

10. The compound according to claim 1, which is ethyl 6-fluoro-4-oxo-1-phenyl-7-(1-piperazinyl)-4H-(1,3)-thiazeto-(3,2-a)quinoline-3-carboxylate or a pharmaceutically acceptable salt thereof.

11. The compound according to claim 1, which is ethyl 6-fluoro-8-methoxy-1-methyl-7-(4-methyl-1-piperazinyl);4-oxo-4H-(1,3)thiazeto(3,2-a)quinoline-3-carboxylate or a pharmaceutically acceptable salt thereof.

12. The compound according to claim 1, which is 6-fluoro-8-methoxy-1-methyl-7-(4-methyl-1-piperazinyl)-4-oxo-4H-(1,3)-thiazeto(3,2-a)quinoline-3-carboxylic acid or a pharmaceutically acceptable salt thereof.

13. The compound according to claim 1, which is 6-fluoro-7-(4-methyl-1-piperazinyl)-4-oxo-1-phenyl-4H-(1,3)-thiazeto-(3,2-a)-quinoline-3-carboxylic acid or a pharmaceutically acceptable salt thereof.

14. The compound according to claim 1, which is ethyl 6-fluoro-7-(4-methyl-1-piperazinyl)-4-oxo-1-phenyl-4H-(1,3)-thiazeto(3,2-a)quinoline-3-carboxylate or a pharmaceutically acceptable salt thereof.

15. The compound according to claim 1, which is ethyl 6-fluoro-8-methoxy-1-methyl-4-oxo-7-(1-piperazinyl)-4H-(1,3)-thiazeto-(3,2-a)quinoline-3-carboxylate or a pharmaceutically acceptable salt thereof.

16. The compound according to claim 5, wherein said salt is the methanesulfonate, hydrochloride or maleate.

17. The compound according to claim 6, wherein said salt is the methanesulfonate, hydrochloride or maleate.

18. The compound according to claim 7, wherein said salt is the methanesulfonate, hydrochloride or maleate.

19. The compound according to claim 9, wherein said salt is the methanesulfonate, hydrochloride or maleate.

20. The compound according to claim 13, wherein said salt is the methanesulfonate, hydrochloride or maleate.

21. The compound according to claim 1 which is 6-fluoro-7-(4-methyl-1-piperazinyl)-4-oxo-4H-(1,3)thiazeto(3,2-a)-quinoline-3-carboxylic acid.

22. The compound according to claim 1 which is 6-fluoro-1-methyl-7-(4-methyl-1-piperazinyl)-4-oxo-4H-(1,3)thiazeto(3,2-a)quinoline-3-carboxylic acid.

23. The compound according to claim 1 which is ethyl 7-(3,4-dimethyl-1-piperazinyl)-6-fluoro-1-methyl-4-oxo-4H-(1,3)thiazeto(3,2-a)quinoline-3-carboxylate.

24. The compound according to claim 1 which is ethyl 6-fluoro-7-(3-methyl-1-piperazinyl)-4-oxo-1-phenyl-4H-(1,3)thiazeto(3,2-a)quinoline-3-carboxylate.

25. The compound according to claim 1 which is ethyl 7-(3,4-dimethyl-1-piperazinyl)-6-fluoro-4-oxo-1-phenyl-4H-(1,3)thiazeto(3,2-a)quinoline-3-carboxylate.

26. A pharmaceutical composition useful for treating bacterial or fungal infections in humans and animals which comprises a therapeutically effective amount of a compound of the formula I

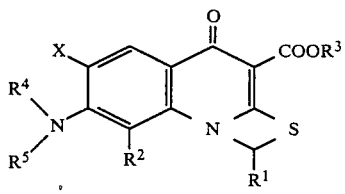

or a pharmaceutically acceptable salt thereof wherein R¹ is hydrogen, straight or branched chain alkyl of 1 to 6 carbon atoms or phenyl unsubstituted or substituted by straight or branched chain alkyl of 1 to 6 carbon atoms, straight or branched chain alkoxy of 1 to 4 carbon atoms, hydroxy, halogen, trifluoromethyl or nitro; R² is hydrogen, straight or branched chain alkyl of 1 to 6 carbon atoms, straight or branched chain alkoxy of 1 to 4 carbon atoms, hydroxy, halogen, nitro or amino unsubstituted or substituted by acyl of 2 to 6 carbon atoms in the acyl moiety; R³ is hydrogen or straight or branched chain alkyl of 1 to 6 carbon atoms unsubstituted or substituted by hydroxy, acyloxy of 2 to 6 carbon atoms or straight or branched chain alkoxy of 1 to 4 carbon atoms; R⁴ and R⁵ together with the nitrogen atom to which they are attached form a piperazinyl ring unsubstituted or substituted by 1 to 3 substituents selected from the group consisting of straight or branched chain alkyl of 1 to 6 carbon atoms, straight or branched chain alkenyl of 2 to 6 carbon atoms, aryl of 6 to 12 carbon atoms, aralkyl of 7 to 12 carbon atoms, hydroxyalkyl wherein the alkyl moiety is straight or branched chain of 1 to 6 carbon atoms, alkoxyalkyl of 2 to 6 carbon atoms or said alkoxyalkyl of 2 to 6 carbon atoms substituted by hydroxyl, aminoalkyl wherein the alkyl moiety is straight or branched chain of 1 to 6 carbon atoms, cyanoalkyl wherein the alkyl moiety is straight or branched chain of 1 to 6 carbon atoms, carboalkoxyalkyl wherein the alkoxy moiety is straight or branched chain of 1 to 4 carbon atoms and the alkyl moiety is straight or branched chain of 1 to 6 carbon atoms, acylalkyl wherein each of the acyl moieties and the alkyl moiety is straight or branched chain of 1 to 6 carbon atoms, acyl of 1 to 6 carbon atoms, hydroxy, oxo, amino, alkylamino wherein the alkyl moiety is straight or branched chain of 1 to 6 carbon atoms or dialkylamino wherein each alkyl moiety is straight or branched chain of 1 to 6 carbon atoms; and X is halogen, in combination with a pharmaceutically acceptable carrier.

27. A composition according to claim 26 wherein the piperazino ring is unsubstituted or substituted by 1 to 3 substituents selected from the group consisting of straight or branched chain alkyl of 1 to 6 carbon atoms, straight or branched chain alkenyl of 2 to 6 carbon atoms, straight or branched chain alkynyl of 2 to 6 carbon atoms, phenyl, alpha-naphthyl, beta-naphthyl, biphenyl, benzyl, phenethyl, phenylpropyl, naphthylmethyl, hydroxyalkyl of 1 to 4 carbon atoms in the alkyl moiety, alkoxyalkyl of 2 to 6 carbon atoms unsubstituted or substituted by hydroxyl, aminoalkyl of 1 to 4 carbon atoms in the alkyl moiety, cyanoalkyl of 1 to 4 carbon atoms in the alkyl moiety, carboalkoxyalkyl of 1 to 4 carbon atoms in each of the alkoxy and alkyl moieties, acylalkyl of 3 to 10 carbon atoms, acyl of 1 to 6 carbon atoms, hydroxy, oxo, amino and mono- or dialkylamino of 1 to 4 carbon atoms in each alkyl moiety.

28. A composition according to claim 26 wherein R¹ is hydrogen, alkyl of 1 to 6 carbon atoms or phenyl; R² is hydrogen, alkoxy of 1 to 4 carbon atoms or hydroxy; R³ is hydrogen or alkyl of 1 to 6 carbon atoms; and X is fluorine or chlorine.

29. A composition according to claim 26 wherein said piperazine is unsubstituted or substituted by alkyl of from 1 to 4 carbon atoms.

30. A composition according to claim 26 wherein the compound is 7-(4-acetonyl-1-piperazinyl)-6-fluoro-1-methyl-4-oxo-4H-(1,3)-thiazeto(3,2-a)quinoline-3-carboxylic acid or a pharmaceutically acceptably salt thereof.

31. A composition according to claim 26 wherein the compound is 6-fluoro-1-methyl-4-oxo-7-(1-piperazinyl)-4H-(1,3)thiazeto-(3,2-a)quinoline-3-carboxylic acid or a pharmaceutically acceptable salt thereof.

32. A composition according to claim 26 wherein the compound is ethyl 6-fluoro-1-methyl-4-oxo-7-(1-piperazinyl)-4H-(1,3)-thiazeto(3,2-a)quinoline-3-carboxylate or a pharmaceutically acceptable salt thereof.

33. A composition according to claim 26 wherein the compound is ethyl 7-(4-acetonyl-1-piperazinyl)-6-fluoro-1-methyl-4-oxo-4H(1,3)-thiazeto(3,2-a)quinoline-3-carboxylate or a pharmaceutically acceptable salt thereof.

34. A composition according to claim 26 wherein the compound is 6-fluoro-1-phenyl-4-oxo-7-(1-piperazinyl)-4H-(1,3)-thiazeto(3,2-a)quinoline-3-carboxylic acid or a pharmaceutically acceptable salt thereof.

35. A composition according to claim 26 wherein the compound is ethyl 6-fluoro-4-oxo-1-phenyl-7-(1-piperazinyl)-4H-(1,3)-thiazeto(3,2-a)quinoline-3-carboxylate or a pharmaceutically acceptable salt thereof.

36. A composition according to claim 26 wherein the compound is ethyl 6-fluoro-8-methoxy-1-methyl-7-(4-methyl-1-piperazinyl)-4-oxo-4H-(1,3)-thiazeto(3,2-a)quinoline-3-carboxylate or a pharmaceutically acceptable salt thereof.

37. A composition according to claim 26 wherein the compound is 6-fluoro-8-methoxy-1-methyl-7-(4-methyl-1-piperazinyl)-4-oxo-4H-(1,3)-thiazeto(3,2-a)quinoline-3-carboxylic acid or a pharmaceutically acceptable salt thereof.

38. A composition according to claim 26 wherein the compound is 6-fluoro-7-(4-methyl-1-piperazinyl)-4-oxo-1-phenyl-4H-(1,3)-thiazeto(3,2-a)quinoline-3-carboxylic acid or a pharmaceutically acceptable salt thereof.

39. A composition according to claim 26 wherein the compound is ethyl 6-fluoro-7-(4-methyl-1-piperazinyl)-4-oxo-1-phenyl-4H-(1,3)-thiazeto(3,2-a)quinoline-3-carboxylate or a pharmaceutically acceptable salt thereof.

40. A composition according to claim 26 wherein the compound is ethyl 6-fluoro-8-methoxy-1-methyl-4-oxo-7-(1-piperazinyl)-4H-(1,3)-thiazeto(3,2-a)quinoline-3-carboxylate or a pharmaceutically acceptable salt thereof.

41. A composition according to claim 30 wherein said salt is the methanesulfonate, hydrochloride or maleate.

42. A composition according to claim 31 wherein said salt is the methanesulfonate, hydrochloride or maleate.

43. A composition according to claim 32 wherein said salt is the methanesulfonate, hydrochloride or maleate.

44. A composition according to claim 33 wherein said salt is the methanesulfonate, hydrochloride or maleate.

45. A composition according to claim 34 wherein said salt is the methanesulfonate, hydrochloride or maleate.

46. A composition according to claim 26 wherein the compound is is 6-fluoro-7-(4-methyl-1-piperazinyl)-4-oxo-4H-(1,3)thiazeto(3,2-a)-quinoline-3-carboxylic acid.

47. A composition according to claim 26 wherein the compound is 6-fluoro-1-methyl-7-(4-methyl-1-piperazinyl)-4-oxo-4H-(1,3)thiazeto(3,2-a)quinoline-3-carboxylic acid.

48. A composition according to claim 26 wherein the compound is ethyl 7-(3,4-dimethyl-1-piperazinyl)-6-fluoro-1-methyl-4-oxo-4H-(1,3)thiazeto(3,2-a)quinoline-3-carboxylate.

49. A composition according to claim 26 wherein the compound is ethyl 6-fluoro-7-(3-methyl-1-piperazinyl)-4-oxo-1-phenyl-4H-(1,3)thiazeto(3,2-a)quinoline-3-carboxylate.

50. A composition according to claim 26 wherein the compound is ethyl 7-(3,4-dimethyl-1-piperazinyl)-6-fluoro-4-oxo-1-phenyl-4H-(1,3)thiazeto(3,2-a)quinoline-3-carboxylate.

51. A method of treating bacterial or fungal infections in humans and animals which comprises administering to a human or animal in need thereof a therapeutically effective amount of a compound of the formula I

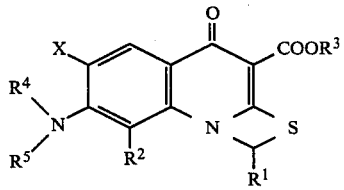

or a pharmaceutically acceptable salt thereof wherein $R^1$ is hydrogen, straight or branched chain alkyl of 1 to 6 carbon atoms or phenyl unsubstituted or substituted by straight or branched chain alkyl of 1 to 6 carbon atoms, straight or branched chain alkoxy of 1 to 4 carbon atoms, hydroxy, halogen, trifluoromethyl or nitro; $R^2$ is hydrogen, straight or branched chain alkyl of 1 to 6 carbon atoms, straight or branched chain alkoxy of 1 to 4 carbon atoms, hydroxy, halogen, nitro or amino unsubstituted or substituted by acyl of 2 to 6 carbon atoms in the acyl moiety; $R^3$ is hydrogen or straight or branched chain alkyl of 1 to 6 carbon atoms unsubstituted or substituted by hydroxy, acyloxy of 2 to 6 carbon atoms or straight or branched chain alkoxy of 1 to 4 carbon atoms; $R^4$ and $R^5$ together with the nitrogen atom to which they are attached form a piperazinyl ring unsubstituted or substituted by 1 to 3 substituents selected from the group consisting of straight or branched chain alkyl of 1 to 6 carbon atoms, straight or branched chain alkenyl of 2 to 6 carbon atoms, straight or branched chain alkynyl of 2 to 6 carbon atoms, aryl of 6 to 12 carbon atoms, aralkyl of 7 to 12 carbon atoms, hydroxyalkyl wherein the alkyl moiety is straight or branched chain of 1 to 6 carbon atoms, alkoxyalkyl of 2 to 6 carbon atoms or said alkoxyalkyl of 2 to 6 carbon atoms substituted by hydroxyl, aminoalkyl wherein the alkyl moiety is straight or branched chain of 1 to 6 carbon atoms, cyanoalkyl wherein the alkyl moiety is straight or branched chain of 1 to 6 carbon atoms, carboalkoxyalkyl wherein the alkoxy moiety is straight or branched chain of 1 to 4 carbon atoms and the alkyl moiety is straight or branched chain of 1 to 6 carbon atoms, acylakyl wherein each of the acyl moieties and the alkyl moiety is straight or branched chain of 1 to 6 carbon atoms, acyl of 1 to 6 carbon atoms, hydroxy, oxo, amino, alkylamino wherein the alkyl moiety is straight or branched chain of 1 to 6 carbon atoms or dialkylamino wherein each alkyl moiety is straight or branched chain of 1 to 6 carbon atoms; and X is halogen, in combination with a pharmaceutically acceptable carrier.

52. The method according to claim 51 wherein the piperazino ring is unsubstituted or substituted by 1 to 3 substituents selected from the group consisting of straight or branched chain alkyl of 1 to 6 carbon atoms, straight or branched chain alkenyl of 2 to 6 carbon atoms, straight or branched chain alkynyl of 2 to 6 carbon atoms, phenyl, alpha-naphthyl, beta-naphthyl, biphenyl, benzyl, phenethyl, phenylpropyl, naphthylmethyl, hydroxyalkyl of 1 to 4 carbon atoms in the alkyl moiety, alkoxyalkyl of 2 to 6 carbon atoms unsubstituted or substituted by hydroxyl, aminoalkyl of 1 to 4 carbon atoms in the alkyl moiety, cyanoalkyl of 1 to 4 carbon atoms in the alkyl moiety, carboalkoxyalkyl of 1 to 4 carbon atoms in each of the alkoxy and alkyl moieties, acylalkyl of 3 to 10 carbon atoms, acyl of 1 to 6 carbon atoms, hydroxy, oxo, amino and mono- or dialkylamino of 1 to 4 carbon atoms in each alkyl moiety.

53. A method according to claim 51 wherein $R^1$ is hydrogen, alkyl of 1 to 6 carbon atoms or phenyl; $R^2$ is hydrogen, alkoxy of 1 to 4 carbon atoms or hydroxy; $R^3$ is hydrogen or alkyl of 1 to 6 carbon atoms; and X is fluorine or chlorine.

54. A method according to claim 51 wherein said piperazine is unsubstituted or substituted by alkyl of from 1 to 4 carbon atoms.

55. A method according to claim 51 wherein the compound is 7-(4-acetonyl-1-piperazinyl)-6-fluoro-1-methyl-4-oxo-4H-(1,3)-thiazeto(3,2-a)quinoline-3-carboxylic acid or a phramceutically acceptably salt thereof.

56. A method according to claim 51 wherein the compound is 6-fluoro-1-methyl-4-oxo-7-(1-piperazinyl)-4H-(1,3)thiazeto-(3,2-a)quinoline-3-carboxylic acid or a pharmaceutically acceptable salt thereof.

57. A method according to claim 51 wherein the compound is ethyl 6-fluoro-1-methyl-4-oxo-7-(1-piperazinyl)-4H-(1,3)-thiazeto(3,2-a)quinoline-3-carboxylate or a pharmaceutically acceptable salt thereof.

58. A method according to claim 51 wherein the compound is ethyl 7-(4-acetonyl-1-piperazinyl)-6-fluoro-1-methyl-4-oxo-4H(1,3)-thiazeto(3,2-a)quinoline-3-carboxylate or a pharmaceutically acceptable salt thereof.

59. A method according to claim 51 wherein the compound is 6-fluoro-1-phenyl-4-oxo-7-(1-piperazinyl)-4H-(1,3)-thiazeto(3,2-a)quinoline-3-carboxylic acid or a pharmaceutically acceptable salt thereof.

60. A method according to claim 51 wherein the compound is ethyl 6-fluoro-4-oxo-1-phenyl-7-(1-piperazinyl)-4H-(1,3)-thiazeto(3,2-a)quinoline-3-carboxylate or a pharmaceutically acceptable salt thereof.

61. A method according to claim 51 wherein the compound is ethyl 6-fluoro-8-methoxy-1-methyl-7-(4-methyl-1-piperazinyl)-4-oxo-4H-(1,3)thiazeto(3,2-a)quinoline-3-carboxylate or a pharmaceutically acceptable salt thereof.

62. A method according to claim 51 wherein the compound is 6-fluoro-8-methoxy-1-methyl-7-(4-methyl-1-piperazinyl)-4-oxo-4H-(1,3)-thiazeto(3,2-a)quinoline-3-carboxylic acid or a pharmaceutically acceptable salt thereof.

63. A method according to claim 51 wherein the compound is 6-fluoro-7-(4-methyl-1-piperazinyl)-4-oxo-1-phenyl-4H-(1,3)-thiazeto(3,2-a)quinoline-3-carboxylic acid or a pharmaceutically acceptable salt thereof.

64. A method according to claim 51 wherein the compound is ethyl 6-fluoro-7-(4-methyl-1-piperazinyl)-4-oxo-1-phenyl-4H-(1,3)-thiazeto(3,2-a)quinoline-3-carboxylate or a pharmaceutically acceptable salt thereof.

65. A method according to claim 51 wherein the compound is ethyl 6-fluoro-8-methoxy-1-methyl-4-oxo-7-(1-piperazinyl)-4H-(1,3)-thiazeto(3,2-a)quinoline-3-carboxylate or a pharmaceutically acceptable salt thereof.

66. A method according to claim 55 wherein said salt is the methanesulfonate, hydrochloride or maleate.

67. A method according to claim 56 wherein said salt is the methanesulfonate, hydrochloride or maleate.

68. A method according to claim 57 wherein said salt is the methanesulfonate, hydrochloride or maleate.

69. A method according to claim 58 wherein said salt is the methanesulfonate, hydrochloride or maleate.

70. A method according to claim 59 wherein said salt is the methanesulfonate, hydrochloride or maleate.

71. A method according to claim 51 wherein the compound is is 6-fluoro-7-(4-methyl-1-piperazinyl)-4-oxo-4H-(1,3)thiazeto(3,2-a)-quinoline-3-carboxylic acid.

72. A method according to claim 51 wherein the compound is 6-fluoro-1-methyl-7-(4-methyl-1-piperazinyl)-4-oxo-4H-(1,3)thiazeto(3,2-a)quinoline-3-carboxylic acid.

73. A method according to claim 51 wherein the compound is ethyl 7-(3,4-dimethyl-1-piperazinyl)-6-fluoro-1-methyl-4-oxo-4H-(1,3)thiazeto(3,2-a)quinoline-3-carboxylate.

74. A method according to claim 51 wherein the compound is ethyl 6-fluoro-7-(3-methyl-1-piperazinyl)-4-oxo-1-phenyl-4H-(1,3)thiazeto(3,2-a)quinoline-3-carboxylate.

75. A method according to claim 51 wherein the compound is ethyl 7-(3,4-dimethyl-1-piperazinyl)-6-fluoro-4-oxo-1-phenyl-4H-(1,3)thiazeto(3,2-a)quinoline-3-carboxylate.

* * * * *

UNITED STATES PATENT AND TRADEMARK OFFICE
CERTIFICATE OF CORRECTION

PATENT NO. : 4,843,070

DATED : JUNE 27, 1989

INVENTOR(S) : Masahiro Kise, Masahiko Kitano, Masakuni Ozaki, Kenji Kazuno, Ichiro Shirahase, Yoshifumi Tomii, Jun Segawa It is certified that error appears in the above-identified patent and that said Letters Patent is hereby corrected as shown below:

Column 2, lines 15 and 16, change "acetyl, propionyl, n-butyryl, isobutyryl, valeryl, isovaleryl, pivaloyl, n-hexanoyl" to -- such as acetyloxy, propionyloxy, n-butyryloxy, isobutyryloxy, valeryloxy, isovaleryloxy, pivaloyloxy, n-hexanoyloxy --.

Column 3, line 6, change "$R^2$" to -- $R^3$ --.

Column 11, line 15, after "27.56" insert -- g --.

Signed and Sealed this

Twenty-fifth Day of February, 1992

Attest:

HARRY F. MANBECK, JR.

*Attesting Officer*  *Commissioner of Patents and Trademarks*